(12) United States Patent
Kozmin et al.

(10) Patent No.: US 8,350,062 B2
(45) Date of Patent: Jan. 8, 2013

(54) SYNTHESIS AND ANTICANCER ACTIVITY OF NEW ACTIN-TARGETING SMALL-MOLECULE AGENTS

(75) Inventors: Sergey A. Kozmin, Lake Forest, IL (US); Syed Rizvi, Chicago, IL (US)

(73) Assignee: The University of Chicago, Chicago, IL (US)

( * ) Notice: Subject to any disclaimer, the term of this patent is extended or adjusted under 35 U.S.C. 154(b) by 355 days.

(21) Appl. No.: 12/707,383

(22) Filed: Feb. 17, 2010

(65) Prior Publication Data

US 2010/0217019 A1 Aug. 26, 2010

Related U.S. Application Data

(60) Provisional application No. 61/154,155, filed on Feb. 20, 2009.

(51) Int. Cl.
C07D 493/00 (2006.01)
(52) U.S. Cl. .................................................. 549/343
(58) Field of Classification Search ................ 549/343
See application file for complete search history.

(56) References Cited

PUBLICATIONS

Riou et DN 121:363 (1993) RN 155660-92-7.*
Van Troys, M. et al., "Actin and Actin-Binding Proteins in Cancer Progression and Metastasis", C. Protein Rev. 8, Springer Science and Business Media, LLC: New York, NY, 2008, pp. 229-277.
Fenteany, G. et al., "Small-Molecule Inhibitors of Actin Dynamics and Cell Motility", Curr. Topics Med. Chem.. 2003, 3, pp. 593-616.
Spector, I. et al., "New Anti-Actin Drugs in the Study of the Organization and Function of the Actin Cytoskeleton", Microsc. Res. Tech. 1999, 47, pp. 18-37.
Allingham, J. S. et al., "Actin-targeting natural products: structures, properties and mechanisms of action", Cell. Mol. Life, Sci. 2006, 63, pp. 2119-2134.
Degnan, B. et al., "Novel Cytotoxic Compounds from the Ascidian Lissoclinum bistratum", J. Med. Chem. 1989, 32, pp. 1354-1359.
Murphy, B. T. et al., "Antiproliferative Bistramides from Trididemnum Cyclops from Madagascar", J. Nat. Prod. 2009, 72, pp. 1338-1340.
Statsuk, A. V. et al., "Actin is the primary cellular receptor of bistramide A", Nat. Chem. Biol. 2005, 1, pp. 383-388.
Rizvi, S. A. et al., "Structure of Bistramide A-Actin Complex at a 1.35 A Resolution", J. Am. Chem. Soc., 2006, 128, pp. 3882-3883.
Kritzer, J. A. et al., "Helical β-Peptide Inhibitors of the p53-hDM2 Interaction", J. Am. Chem. Soc., 2004, 126, pp. 9468-9469.
Marjanovic, J. et al., "Spirofungin A: Stereoselective Synthesis and Inhibition of Isoleucyl-tRNA Synthetase", Angew. Chem. Int. Ed. 2007, 46, pp. 8854-8857.
Matsumoto, K. et al., "Eight-Step Synthesis of Routiennocin", Adv. Synth. Catal. 2008, 350, pp. 557-560.
Chatterjee, A. K. et al., "Synthesis of Functionalized Olefins by Cross and Ring-Closing Metatheses", J. Am. Chem. Soc., 2000, 122, pp. 3783-3784.
Wipf, P. et al., "Total Synthesis of a Stereoisomer of Bistramide C and Assignment of Configuration of the Natural Product", Chem. Eur. J. 2002, 8, pp. 1670-1681.
Wipf, P. et al., "Total synthesis and structure validation of (+)-bistramide C", Chem. Commun. 2005, pp. 3421-3423.
Crimmins, M.T. et al., "Enantioselective Total Synthesis of Bistramide A", J. Am. Chem. Soc. 2006, 128, pp. 4936-4937.
Lowe, J.T. et al., "Total Synthesis of Bistramide A", Org. Lett. 2007, 9, pp. 327-330.
Yadav, J.S. et al. "Stereoselective Total Synthesis of Bistramide A", Org. Lett. 2007, 9, pp. 4587-4589.
Wrona, I.E .et al., "Synthesis of a 35-Member Stereoisomer Library of Bistramide a: Evaluation of effects on actin State, Cell Cycle and Tumor Cell Growth", J. Org. Chem.. 2009, 74, pp. 1897-1916.
Amann, K.J. et al., "Direct Real-Time Observation of Actin Filament Branching Mediated by Arp2/3 Complex Using Total Internal Reflection Fluorescence Microscopy", Natl. Acad. Sci. U.S.A. 2001, 98, pp. 15009-15013.
Kovar D. R. et al., "Insertional Assembly of Actin Filament Barbed Ends in Association with Formins Produces Piconewton Forces", Natl. Acad. Sci U.S.A. 2004, 101, pp. 14725-14730.
Kovar D.R. et al., "Control of the Assembly of ATP- and ADP-Actin by Formins and Profilin", Cell, 2006, 124, pp. 423-435.
Neidt E.M. et al., "The Cytokinesis Formins from the Nematode worm and Fission Yeast Differentially Mediate Actin Filament Assembly", J. Biol. Chem. 2008, 283, pp. 23872-23883.
Bhattacharjee, A. et al., "Synthesis of the C1-C21 (C1'-C21') Fragment of the Dimeric Polyketide Natural Product SCH 351448", Org. Lett. 4, pp. 481-484.
Gouiffès D. et al., "Proton Nuclear Magnetic Study of Bistramide A, a new cytotoxic drug isolated from Lissoclinum Bistratum Sluiter", Tetrahedron 1998, 44, pp. 451-459.
Biard, J. et al., "Bistramides A, B, C, D, and K: A New Class of Bioactive Cyclic Polyethers from Lissoclinum Bistratum", J. Natl. Prod. 1994, 57, pp. 1336-1345.
Riou, D. et al., "Comparative Study of the Antitumor Activity of Bistramides A, D and K Against a Non-Small Cell broncho-Pulmonary Carcinoma", 1993, Anticancer Research 13 pp. 2331-2334.
Rizvi S.A. et al., "The dual mode of action of bisramide A entails severing of filamentous actin and covalent protein modification", 2008, PNAS 105, pp. 4088-4092.

* cited by examiner

*Primary Examiner* — Andrew D Kosar
*Assistant Examiner* — Raymond Covington
(74) *Attorney, Agent, or Firm* — Brinks Hofer Gilson & Lione

(57) ABSTRACT

The present invention provides bistramide analogs useful for treating various types of cancer.

2 Claims, No Drawings

SYNTHESIS AND ANTICANCER ACTIVITY OF NEW ACTIN-TARGETING SMALL-MOLECULE AGENTS

RELATED APPLICATIONS

The present application claims priority to U.S. Provisional Patent Application No. 61/154,155, filed Feb. 20, 2009, the entirety of which is hereby incorporated by reference.

BACKGROUND

Small molecules that bind to monomeric or filamentous actin elicit their antiproliferative effects by impairing the ability of cells to progress through the cell cycle and undergo cytokinesis due to the defective actin cytoskeleton. Understanding the mode of action of such compounds expands our knowledge of actin biochemistry and provides opportunities for the development of new therapeutic agents. Traditionally, studies of the mechanism of action of small-molecule modulators of actin polymerization entailed the investigations of changes in fluorescence intensity during polymerization or depolymerization of pyrene- or prodan-labeled actin in solution. However, the main limitation of this method arises from the fact that the changes in the fluorescence intensity may reflect the binding of a small molecule to the filaments, especially if the binding event occurs in the close proximity to the dye, resulting in quenching of fluorescence, which could be independent of the rates of actin depolymerization. Total internal reflection fluorescence (TIRF) microscopy has recently emerged as a powerful tool to investigate actin filament dynamics and its regulation by several actin-binding proteins, as well as latrunculin A, which is incapable of depolymerizing filamentous actin in vitro. We used TIRF microscopy to directly observe actin filament severing by a series of small molecules, which are derived from bistramide A—a marine natural product that specifically and potently targets actin in the cell (Statsuk, et al. (2005) *Nat Chem Biol* 1:383-388; incorporated by reference). In addition, we demonstrated that the C(1)-C(4) enone-containing subunit of this natural product plays a pivotal role in covalent modification of cellular actin, which further enhances the cytotoxicity of the corresponding bistramide-based compounds. Our study provides comprehensive characterization of the unique mode of action of bistramide A and identifies structural requirements of bistramides that are responsible for severing actin filaments and inhibiting growth of cancer cells in vitro and in vivo (Gouiffe's, et al. (1998) *Tetrahedron* 44:451-459; Biard, et al. (1994) *J Nat Prod* 57:1336-1345; Riou, et al. (1993) *Anticancer Res* 13:2331-2334; Rizvi et al. (2008) *PNAS* 105: 4088-4092; the entireties of all of which are hereby incorporated by reference).

BRIEF SUMMARY

This application describes a characterization of the mode of action of bistramide A in order to identify structural requirements of bistramide-based compounds that are responsible for severing actin filaments and inhibiting growth of cancer cells in vitro and in vivo. We employed TIRF microscopy to directly observe actin filament severing by a series of bistramide analogs. In addition, we demonstrated that the enone subunit of bistramide A is responsible for covalent modification of the protein in vitro and in A549 cells. Our results revealed a dual biochemical mechanism of action of bistramide A, which entailed both severing of actin filaments and covalent sequestration of monomeric actin in the cell. This work enabled rational design and synthesis of a synthetic analog of the parent natural product, which was effective in inhibiting proliferation of cancer cells in vitro and in vivo.

The present invention provides a novel bistramide analog useful for treating various types of cancer.

DETAILED DESCRIPTION

Design and Synthesis of a Series of Simplified Analogs of Bistramide A

The X-ray structure of bistramide A-actin complex suggested that the C(13)-C(18)-amide and the C(19)-C(38)-spiroketal subunits of the natural product played a dominant role in stabilizing the protein-small molecule interaction via a network of hydrogen-bonding contacts, as well as a series of hydrophobic interactions. To test this prediction, we assembled a series of rationally designed analogs of bistramide A using the same synthetic strategy, which was employed for our synthesis of the parent natural product.

Synthesis of Two Simplified Spiroketal Fragments

Our studies began with the synthesis of two simplified spiroketals shown in Scheme 1. Spiroketal 31 is devoid of the C(23) and C(34) methyl groups and incorporates a truncated side chain following removal of the C(37)-C(40) segment. Spiroketal 32, incorporates both the C23 and C34 methyl group. However, the terminal allylic alcohol fragment is eliminated.

Scheme 1. Simplified spiroketals 31 and 32

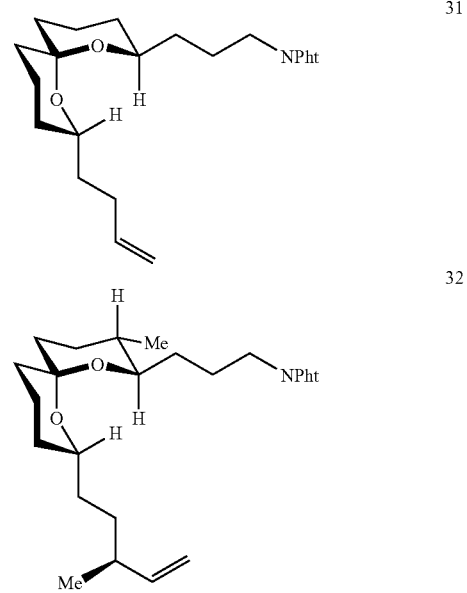

Synthesis of Simplified Spiroketal 31

We envisioned that alkene 31 could be assembled by desymmetrization of the $C_2$ symmetric alcohol 33. Two sequential olefin metathesis reactions of cyclopropenone acetal 10 with two copies of homoallylic alcohol 34 would provide rapid and highly convergent access to this fragment (Scheme 2). The symmetric diol would be desymmetrized at a later stage of the synthesis.

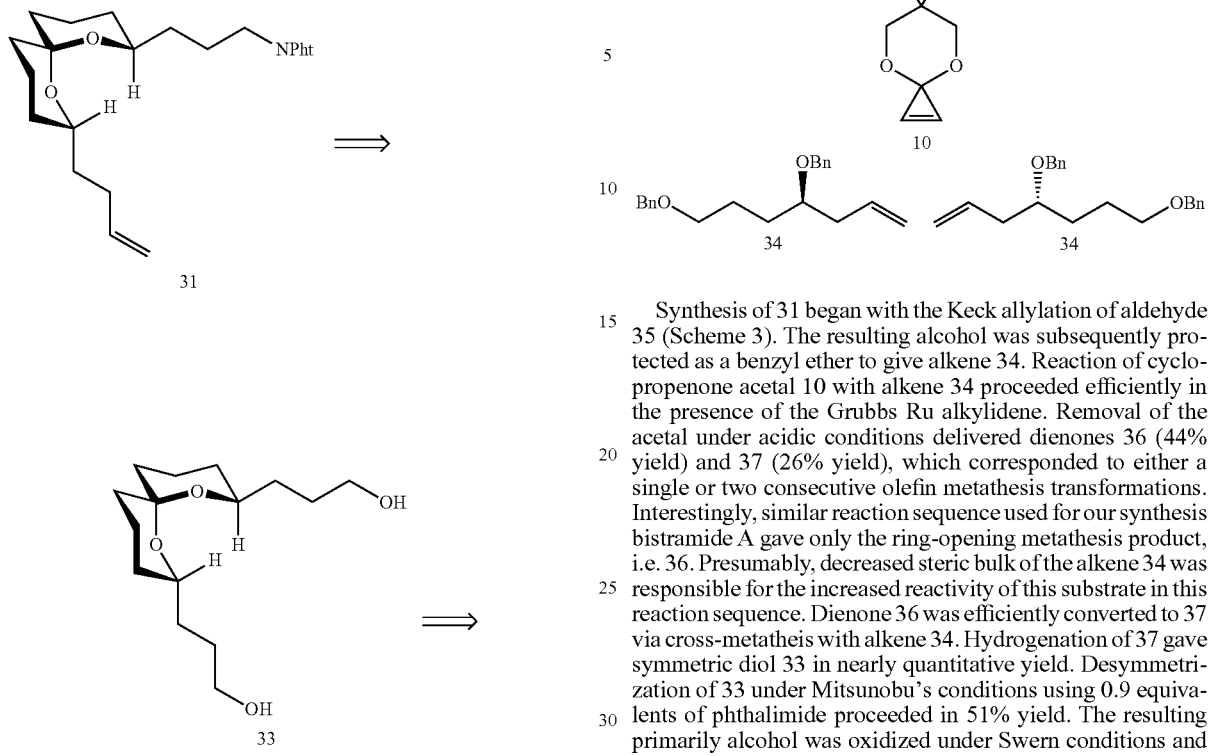

Synthesis of 31 began with the Keck allylation of aldehyde 35 (Scheme 3). The resulting alcohol was subsequently protected as a benzyl ether to give alkene 34. Reaction of cyclopropenone acetal 10 with alkene 34 proceeded efficiently in the presence of the Grubbs Ru alkylidene. Removal of the acetal under acidic conditions delivered dienones 36 (44% yield) and 37 (26% yield), which corresponded to either a single or two consecutive olefin metathesis transformations. Interestingly, similar reaction sequence used for our synthesis bistramide A gave only the ring-opening metathesis product, i.e. 36. Presumably, decreased steric bulk of the alkene 34 was responsible for the increased reactivity of this substrate in this reaction sequence. Dienone 36 was efficiently converted to 37 via cross-metatheis with alkene 34. Hydrogenation of 37 gave symmetric diol 33 in nearly quantitative yield. Desymmetrization of 33 under Mitsunobu's conditions using 0.9 equivalents of phthalimide proceeded in 51% yield. The resulting primarily alcohol was oxidized under Swern conditions and subjected to Wittig methylenation to give the desired spiroketal 31.

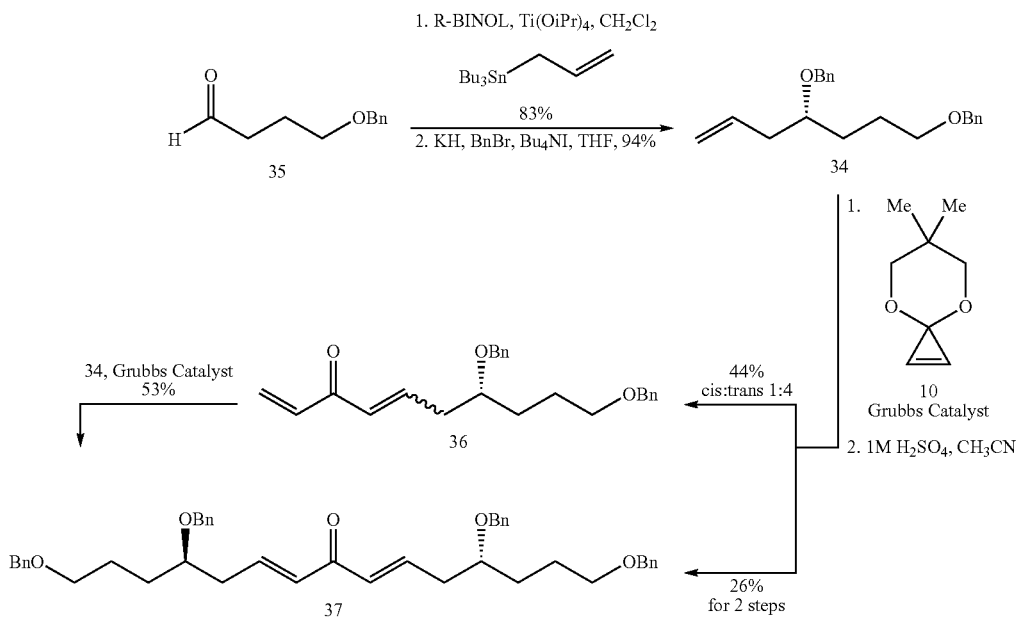

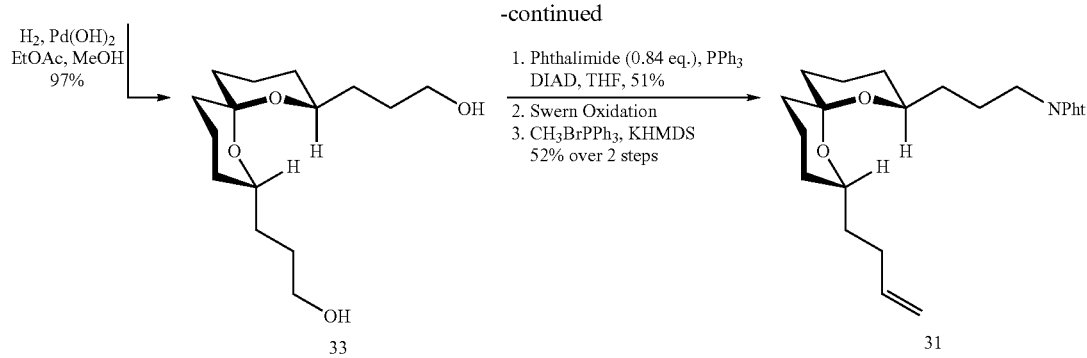

Synthesis of Simplified Spiroketal 32

Synthesis of simplified spiroketal 32 began with a similar sequence of transformations employed for the assembly of bistramide A (Scheme 4). Ring-opening metathesis of cyclopropenone acetal 10 with alkene 38, followed by removal of the acetal with oxalic acid on silica gel gave dienone 39.

Milder acidic conditions for acetal removal were required in order to prevent cleavage of the tert-butyl-di-methylsilyl (TBS) protecting group during this step. Cross-metathesis of dienone 39 with alkene 40 gave chain-extended dienone 41, which upon hydrogenation delivered spiroketal 42. Swern

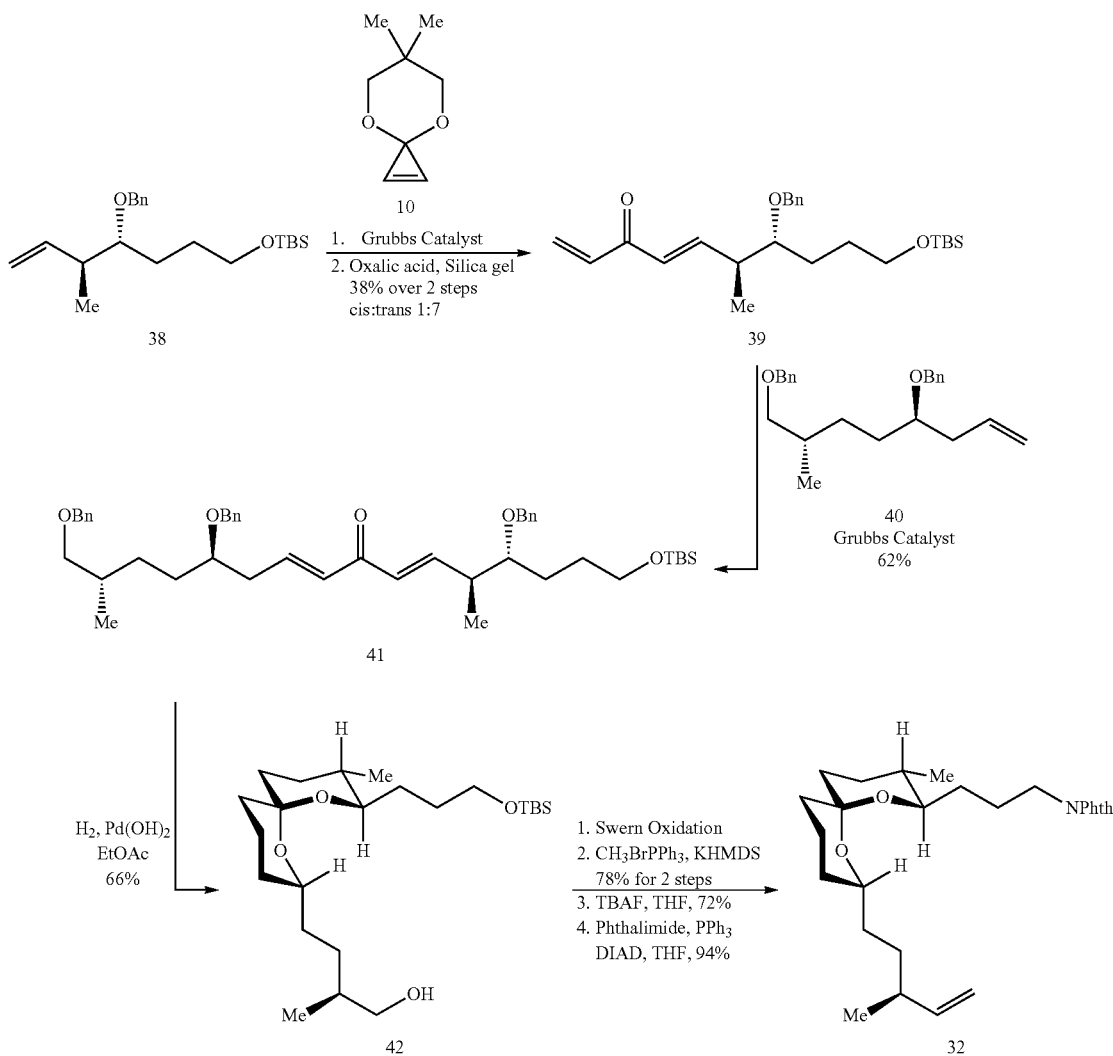

oxidation, Wittig olefination, followed by removal of the TBS group and conversion of the resulting alcohol to phthalimide under Mitsunobu conditions gave the requisite spiroketal 3.

Synthesis of a Simplified Pyran Fragment

In order to probe the effect of the enone moiety in the pyran fragment of bistramide A, we designed a simplified version of this subunit (44) shown in Scheme 5. Synthesis of this compound entailed saponification of previously reported ester 43, which was prepared from Bhattacharjee, A., Soltani, O. & De Brabander, J. K. (2002) *Org. Lett.* 4, 481-484, the entirety of which is hereby incorporated by reference.

Scheme 5. Synthesis of the simplified pyran.

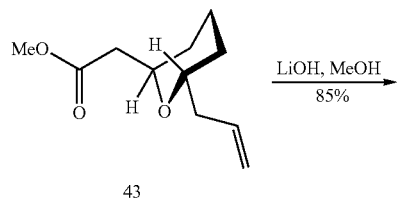

43

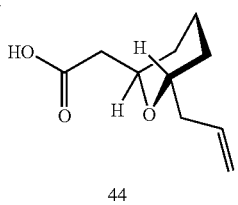

44

Fragment Coupling

Synthesis of analog 3 and analog 6 was carried as shown in Scheme 6. The amino group of spiroketal 31 was deprotected upon treatment with methylamine and coupled with carboxylic acid 7 to give amide 45. Removal of the Fmoc-protecting group and coupling of the resulting amine with activated esters 8 and 46 gave analogs 3 and 6, respectively.

Scheme 6.

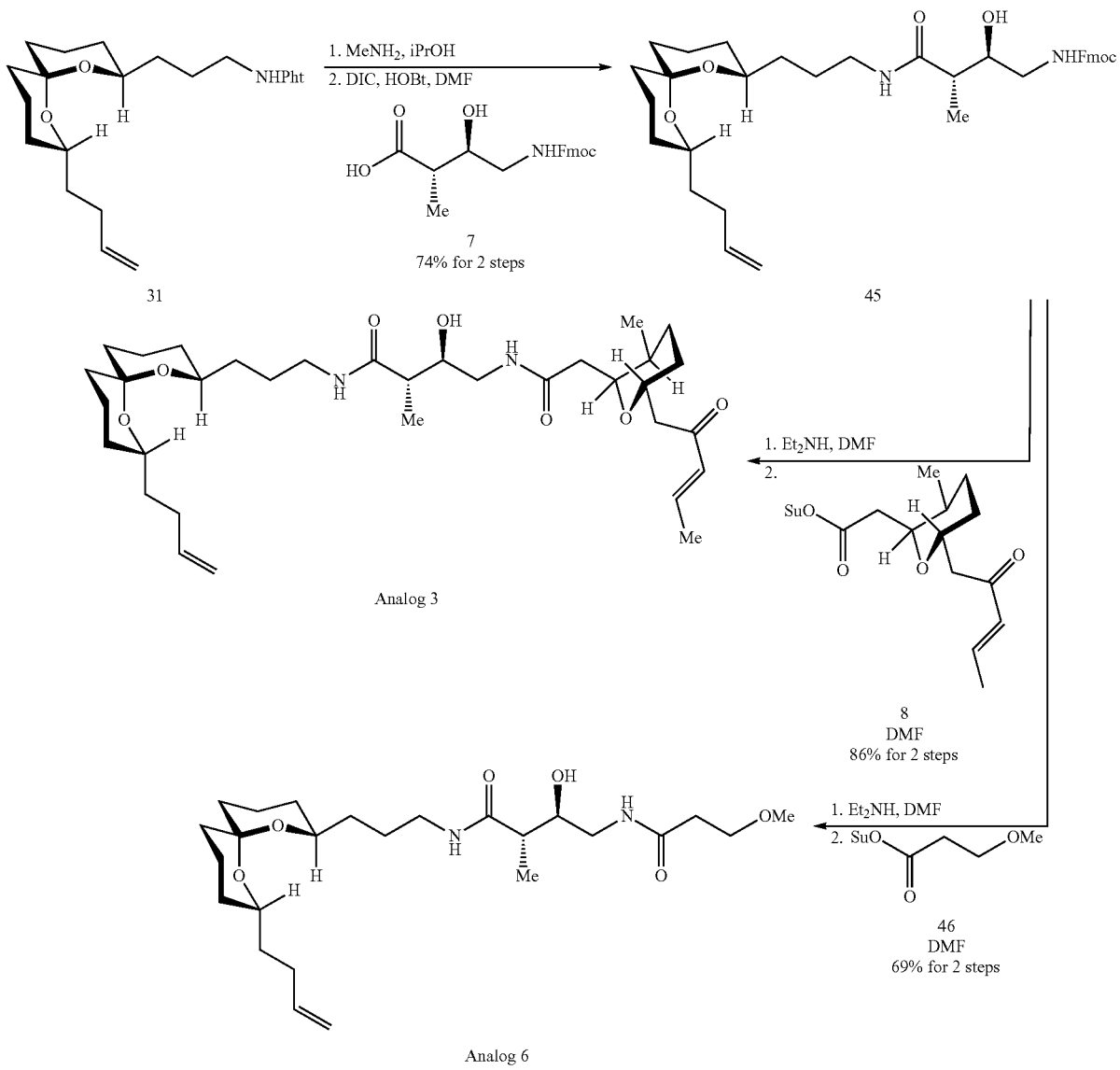

Analogs 2, 4 and 5 were synthesized according to Scheme 7. The amino group of spiroketal 32 was deprotected upon similar conditions and coupled to carboxylic acid 7 to give amide 47. Removal of the Fmoc-protecting group and coupling of the resulting amine with succinimide esters 8 and 46 gave analogs 2, 5 respectively. Alternatively, PyBOP-mediated coupling of the same amine with carboxylic acid 44 gave analog 4.

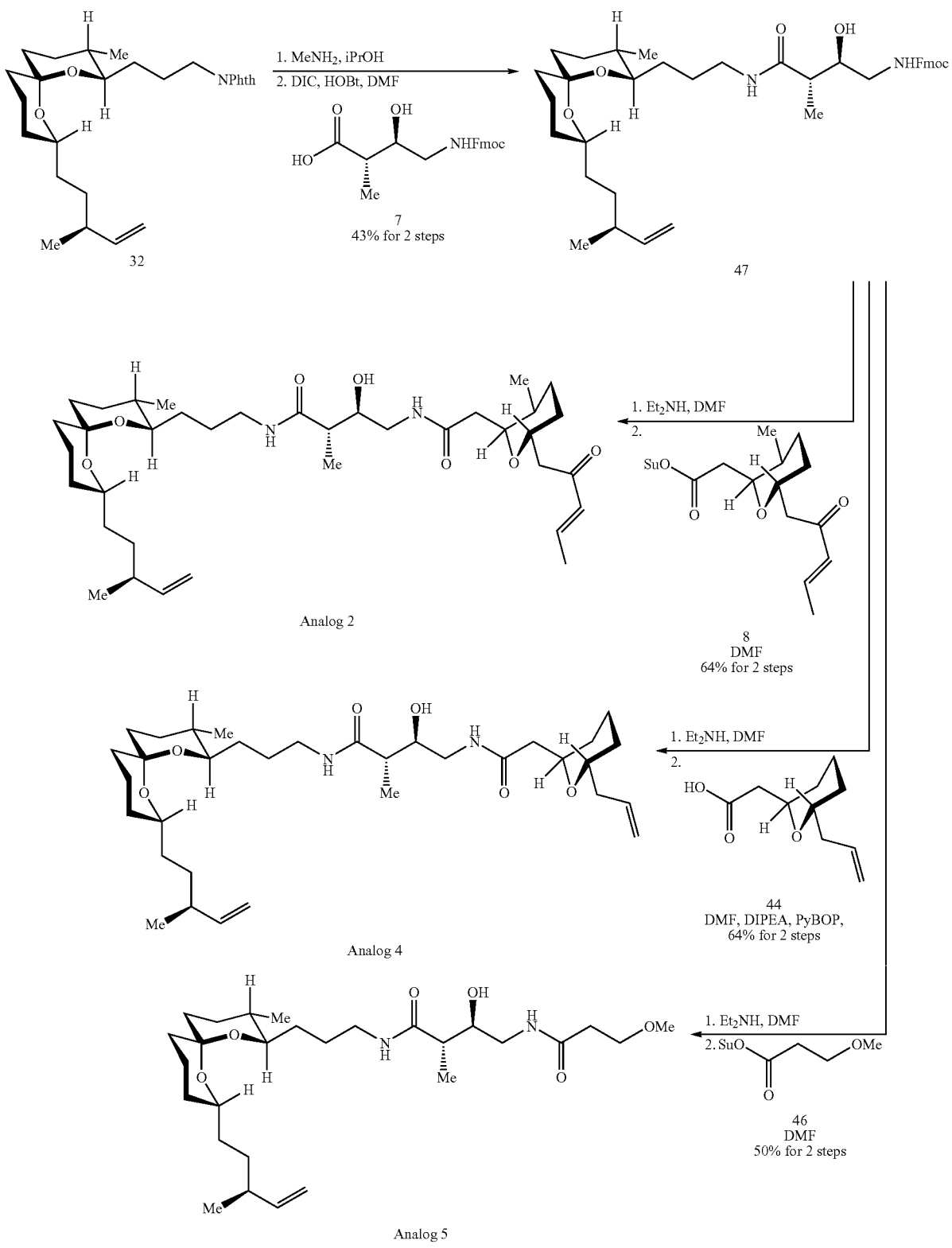

Scheme 7. Synthesis of Analogs 2, 4 and 5

Scheme 8. Synthesis of Analog 7.

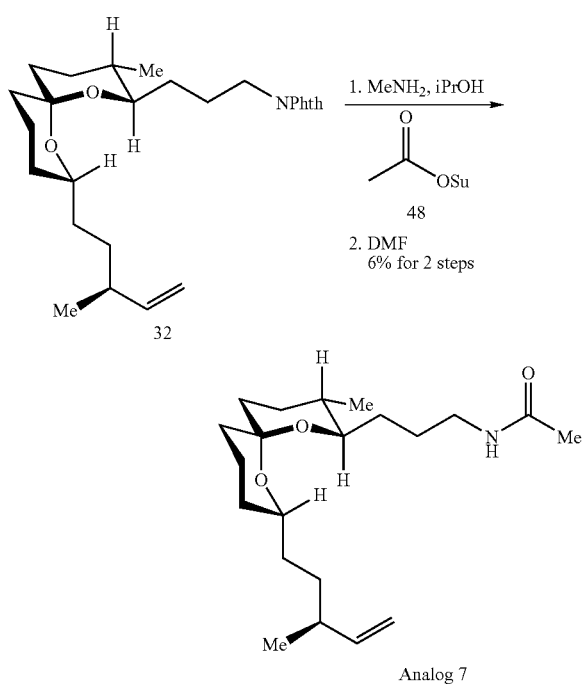

Syntheses of additional analogs (7 and 8) are shown Schemes 12 and 13. Analog 7 was designed to probe the effect of elimination of both the pyran subunit and the central amino acid fragment. This compound was prepared by deprotection of phthalimide 32 with methylamine, followed by coupling of the resulting amine with activated ester 48 (Scheme 8).

Analog 8 was designed to probe the effect of removal of both the pyran and the spiroketal subunits on the activity of the resulting compounds. This compound was prepared coupling of amine 49 with carboxylic acid 7, followed by removal of the Fmoc-deprotection and coupling with ester 46 (Scheme 9).

Actin Binding and Cytotoxicity

We evaluated each of the analogs, as well as the parent natural product, for its ability to bind monomeric actin by isothermal titration calorimetry (ITC) and to inhibit proliferation of A549 cells. We found that neither the spiroketal (analog 7) nor the central amide subunit (analog 8) alone displayed any observable activity. However, when both fragments were linked (analog 5), the in vitro actin binding efficiency was restored to a significant extent ($K_d$=43 nM), indicating that the combination of the spiroketal and the amide subunits represented the minimal structural requirement for G-actin-binding. These observations were consistent with conclusions made on the basis of the X-ray crystallographic data. Furthermore, elimination of the two methyl groups at C(23) and C(34), which participated in hydrophobic interactions with Thr-351, Phe-352, Met-355, Ile-345, Tyr-143, Leu-349 of actin, resulted in substantial loss of actin-binding efficiency (analog 6, $K_d$=680 nM).

However, despite the potent actin-binding affinities of analogs 5 ($K_d$=43 nM) and 6 ($K_d$=680 nM), the two compounds were significantly less potent in inhibiting cell proliferation compared with the parent natural product 1. The $GI_{50}$ value for analog 5 was 15.1 μM whereas analog 6 did not inhibit the growth of A549 cells by 50% at concentrations as high as 100 μM. On the other hand, bistramide A has a $GI_{50}$ value of 20.4 nM.

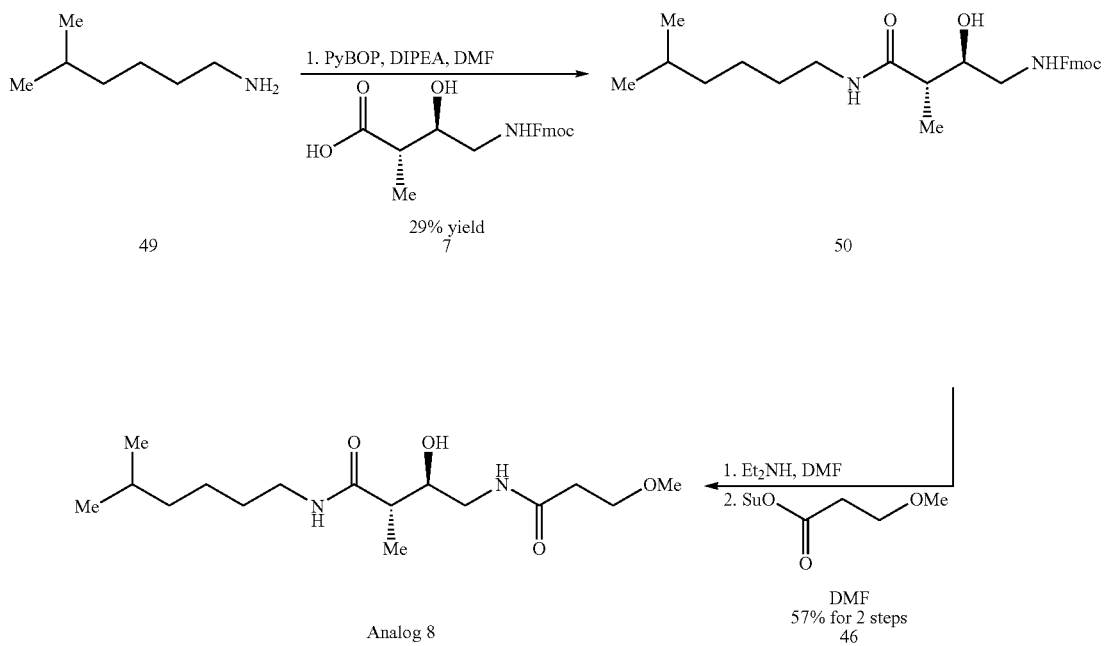

Scheme 9. Synthesis of Analog 8.

TABLE 1

Binding constants and cytotoxicity of bistramide analogs

| Compound | $K_d$ (nM) | $GI_{50}$ (μM) |
|---|---|---|
| Bistramide A (1) | 7 | 0.020 |
| Analog 2 | 70 | 0.087 |
| Analog 3 | 1500 | 0.323 |
| Analog 4 | 319 | 11.2 |
| Analog 5 | 43 | 15.1 |
| Analog 6 | 680 | No cell-based activity |
| Analog 7 | No actin binding | No cell-based activity |
| Analog 8 | No actin binding | No cell-based activity |

Introduction of the C(4)-C(13) pyran subunit (analog 4, $GI_{50}$=11.2 μM) did not have significant effects on actin-binding and cell-based activity. However, incorporation of the C(1)-C(4) enone moiety in analogs 2 ($GI_{50}$=87.1 nM) and 3 ($GI_{50}$=323 nM) restored potent cell-based activity without any significant increase in G-actin binding. Interestingly, analog 2 inhibited cell growth more effectively compared with analog 5, whereas the G actin-binding affinities of the two compounds were reversed. This observation suggested for the first time that the C(1)-C(4) enone subunit played a critical role in increasing cytotoxicity of the bistramide-based compounds—a result which could not be rationalized using x-ray crystallographic characterization of the interaction of bistramide A with monomeric actin. It is important to remember that four C-terminal amino acid residues and three carbons and the oxygen of C(1)-C(4) enone were disordered in the crystal structure.

Severing of Filamentous Actin by Bistramide-Based Compounds In Vitro.

To gain further insight into the mode of action of bistramide A, we next investigated the interaction of the natural product and its analogs with filamentous actin. Our group had previously demonstrated that bistramide A rapidly decreased the fluorescence of pyrene-labeled F-actin. Similar observations have been reported for several other actin-binding natural products. However, this effect could provide only limited mechanistic information and may primarily reflect the binding of a small molecule to the filaments in close proximity to the dye and quenching of pyrene fluorescence, which could be independent of the rates of actin depolymerization. Some proteins like myosin and Actin Depolymerizing Factor (ADF)/Cofilin are known to do so. Total internal reflection fluorescence (TIRF) microscopy has recently emerged as a powerful tool to investigate actin filament dynamics and its regulation by several actin-binding proteins, as well as latrunculin A, which is incapable of depolymerizing filamentous actin in vitro. Thus, we decided to employ TIRF microscopy to observe in real time the effects of bistramide-based compounds on actin polymerization in vitro. We believe this is the first instance where TIRF microscopy has been utilized to study the severing of actin filaments by a small molecule. We polymerized G-actin containing 25% of tetramethylrhodamine-functionalized and 10% of biotin-functionalized actin. The resulting actin filaments were immobilized onto the streptavidin-coated glass slides (in a flow cell). Analogs 1-8 were flown through the flow cell and imaged by time-lapse TIRF microscopy. Incubation of filamentous actin with 750 nM bistramide A (1) resulted in rapid filament depletion (Table 2, entry 1). Analysis of the dynamics of this process revealed that each of the compounds induced multiple breaks in actin filaments and did not affect the rates of actin depolymerization at either the barbed or the pointed end (Table 2, entries 4-9).

As expected, analogs 7 and 8 had no effect on actin depolymerization even at concentrations as high as 200 μM. In the presence of these compounds, the decrease in the number and the length of actin filaments was consistent with the kinetics of slow dilution-induced actin disassembly (Table 2, entries 1-3).

Analogs 2, 4 and 5 also severed actin filaments albeit with lesser efficiency as compared to bistramide A (1) (Table 2, entries 6-8). Their actin filament severing efficiency was determined at 15 μM.

Analogs 3 and 6 severed actin filaments only at concentrations as high as 200 μM (Table 2, entries 4-5).

This study demonstrated for the first time that bistramide A was able to rapidly sever actin filaments. Furthermore, analysis of the time-lapse TIRF microscopy images enabled estimation of the relative efficiency of actin severing by bistramide-based analogs, which can be measured by calculating the number of breaks that are observed per 100 μm of actin filaments. This analysis revealed that the combination of C(19)-C(38) spiroketal subunit and the C(13)-C(18) amide segment was sufficient to enable dissolution of actin filaments (Table 2, entries 4, 6 and 7). In addition, incorporation of the C(1)-C(4) enone appeared to increase actin-severing ability of analogs 2 and 3 (Table 2, entries 8 and 5) compared with analogs 4, 5 and 6 (Table 2, entries 7, 6, and 4).

TABLE 2

Real-time observation of actin depolymerization by bistramide-based compounds using TIRF microscopy.

| Entry no. | Compound (Concentration, μM) | No. of breaks per 100 μm | Barbed-end depolymerization rate (subunits/s)[§] | Pointed-end depolymerization rate (subunits/s)[¶] |
|---|---|---|---|---|
| 1 | None | None | 2.07 | 0.37 |
| 2 | Analog 8 (200) | None | 2.15 | 0.21 |
| 3 | Analog 7 (200) | 0.2 | 1.87 | 0.32 |
| 4 | Analog 6 (200) | 3.4 | 2.29 | 0.41 |
| 5 | Analog 3 (200) | 13.3 | 1.84 | 0.57 |
| 6 | Analog 5 (15) | 13.0 | 1.93 | 0.55 |
| 7 | Analog 4 (15) | 16.5 | 1.92 | 0.51 |
| 8 | Analog 2 (15) | 41.8 | 1.90 | 0.48 |
| 9 | Bistramide A (0.75) | 40.4 | 1.88 | 0.49 |

[§]Standard deviations are 0.4-0.6 subunits/s
[¶]Standard deviations are 0.1-0.3 subunits/s To further examine the effect of an enone moiety on the efficiency of severing actin filaments in vitro, we measured the initial rate of severing over a range of concentrations of analogs 2 and 4 (1-15 μM). The number of severing events occurring before the actin on the slide is depleted by 50% was determined. This study unambiguously confirmed that analog 2, which contained the enone moiety, was at least three times more potent at severing filamentous actin.

Actin Depolymerization In A549 Cells.

The presence of the enone increased the severing efficiency of the analogs three-fold. However, this still did not account for the more than 100-fold increase in toxicity of the compounds containing the enone. We determined whether it was the depletion of actin filaments by analogs 2-5 which was responsible for the growth inhibition of A549 cells. Each of the compounds was incubated with A549 cells for 2 h at a concentration that exceeded the $GI_{50}$ value by a factor of 5. The cells were then fixed, permeabilized and filamentous actin was visualized by fluorescence microscopy following Alexa Fluor 488 phalloidin staining. Bistramide A (1), as well as analogs 2 and 3 containing the C(1)-C(4) enone, were found to be significantly more potent at inducing actin depolymerization in A549 cells. They induced depolymerization at 150 nM for bistramide A (1), 500 nM for analog 2 and 2 μM for analog 3. Analogs 4 and 5 induced depolymerization of actin only at concentrations as high as 100 μM. No depolymerization was observed in cells treated with 100 μM analogs 6, 7 and 8. This observation was consistent with the enhanced cell-based activity of the compounds containing the C(1)-C(4) enone moiety.

Covalent Modification of Actin by Enone-Containing Bistramides.

We examined the possibility that the observed increase in cytotoxicity and actin-severing ability of analogs 1, 2, and 3 could be due to the covalent modification of the protein target. We used MALDI-TOF to monitor the interaction of bistramide-based compounds with actin in vitro and found that bistramide A (1) and enone-containing analogs 2 and 3 covalently modified G-actin, resulting in the formation of higher molecular weight peaks.

In contrast, no cross-linking was observed in the case of analogs 4, 5, and 6, which did not contain the enone moiety. Due to the unprecedented high reactivity of Cys-374 we believe that the covalent interaction of bistramide A with actin is a result of the Michael addition of the thiol of Cys-374 to the C(1)-C(4) enone portion of the natural product. This modification could not be observed by x-ray crystallography because the enone portion of bistramide, as well as the four C-terminal amino acids of actin, including Cys-374, was disordered in the crystal.

Synthesis of the Bistramide-BODIPY Conjugate.

Having observed covalent modification of the purified actin by bistramide A (1) and enone-containing analogs 2 and 3, we constructed BODIPY-conjugated bistramide A (analog 9, Schemes 10 and 11) and tested whether the covalent modification of the protein could be detected in A549 cells. Bistramide A (1) was treated with alkene 51 and Grubbs Catalyst to give the bistramide A-azide conjugate 52, which was then subjected to a [3+2] cycloaddition with alkyne-BODIPY conjugate 53 to give the fluorescent bistramide-BODIPY conjugate 9.

Scheme 10. Synthesis of bistramide A-azide conjugate 52

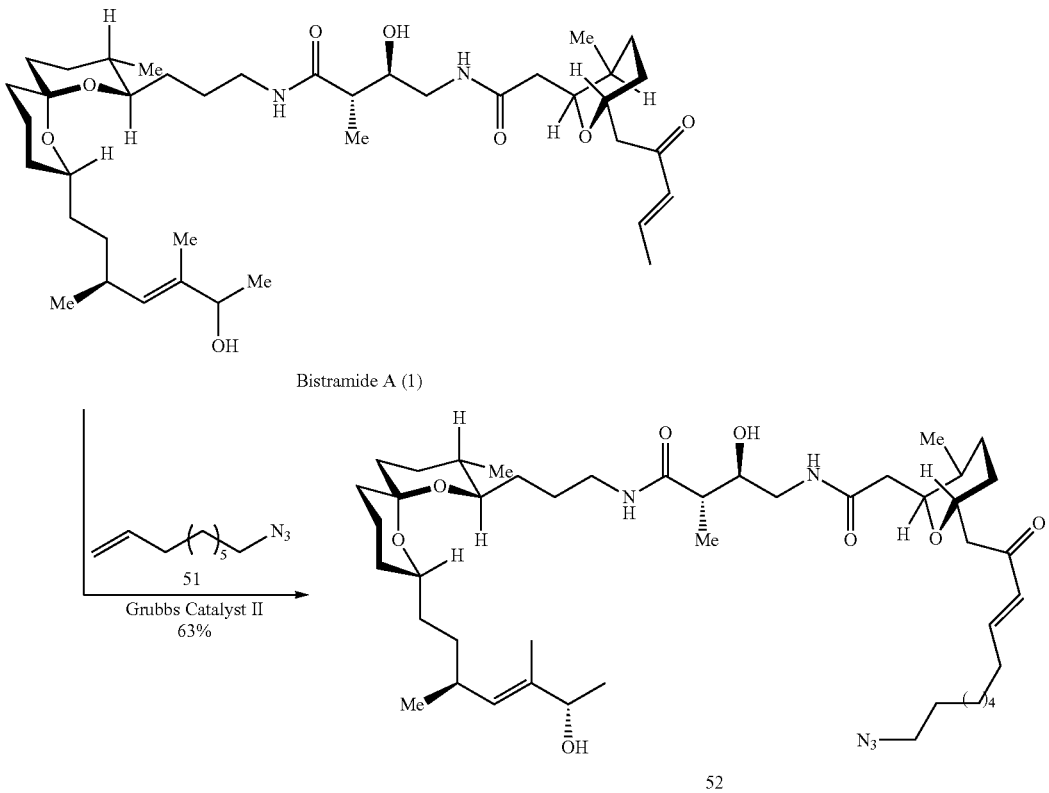

Scheme 11. Synthesis of analog 9

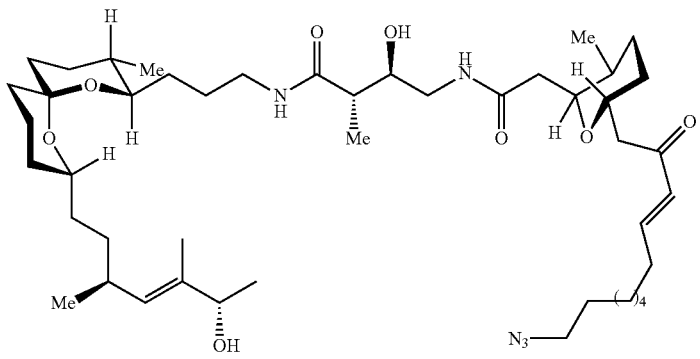

52

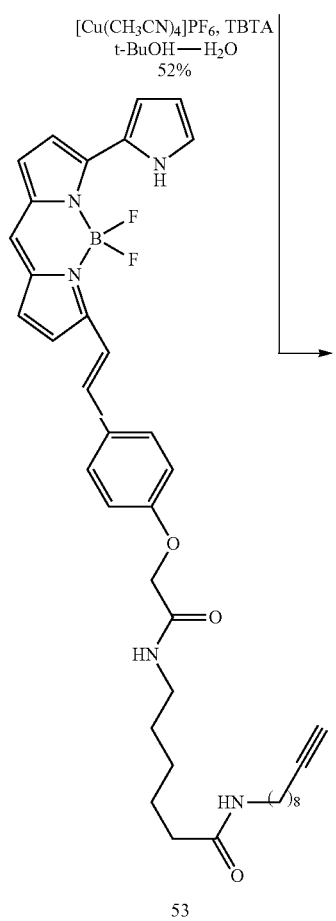

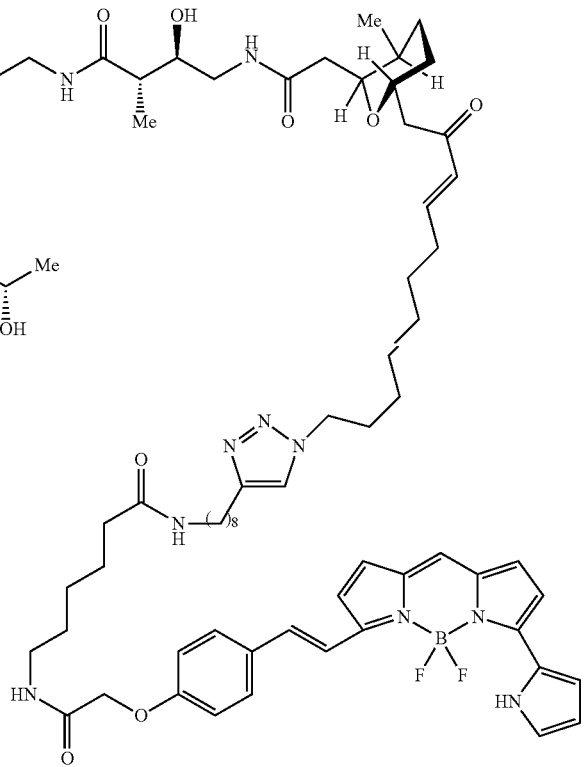

53

Analog 9

Covalent Modification of Actin by the Bistramide-BODIPY Conjugate In Vivo.

Initially, we treated purified actin with analog 9 and established cross-linking of the protein by this chemical probe using MALDI-TOF and fluorescence imaging of the labeled protein on polyacrylamide gel. Next, we incubated A549 cells with analog 9 (5 µM) for 3 h and observed efficient cross-linking of cellular actin, which was detected by fluorescence imaging of the cell lysate on polyacrylamide gel and appeared to be identical to the purified protein. Importantly, no other covalently modified proteins were detected. A combination of MALDI-TOF and fluorescent imaging experiments using probe 9 unambiguously demonstrated that the C(1)-C(4) enone subunit of bistramide A is responsible for efficient cross-linking of actin both in vitro and in live cells Bistramide-Based Synthetic Analog Designed to Target Cancer Cell Growth in Vitro and In Vivo.

Cytoskeletal organization is strongly altered upon malignant transformation and tumor invasion, which includes significant changes in expression of actin and actin-binding proteins. Small molecules that target the actin cytoskeleton could be potentially employed to study such alterations in vivo and ultimately combat cancer. Bistramides comprise a polyketide-based family of marine natural products with potent antiproliferative activities, which was isolated from tunicates L. bistratum and T. cyclops. We have established that actin-severing activity of Bistramide A was not dependent on covalent protein modification. This observation suggested that rationally designed bistramide derivatives, which do not react covalently with actin, may be able to target the actin cytoskeleton of cancer cells in vivo without significant toxic side effects. Indeed, bistramides D and K that lack the reactive enone subunit were shown to inhibit proliferation of non-small cell broncho-pulmonary carcinoma xenografts implanted in nude mice. Here, we describe structure-based design and synthesis of a simplified analog of bistramide A, which potently and reversibly binds monomeric actin, efficiently depolymerizes filamentous actin, inhibits growth of cancer cell lines in vitro and suppresses proliferation of A549 (non-small cell lung cancer) cells in vivo.

The structure of bistramide A can be dissected into three main fragments, including the C(19)-C(38) spiroketal-bearing subunit A, the C(13)-C(18) bisamide subunit B, and the C(1)-C(13) enone-containing subunit C. Subunits A and B are required for binding of the natural product to its target by forming extended networks of hydrogen-bonding and van der Waals interactions, respectively. The 1,3-enone moiety present in subunit C is responsible for covalent interaction of bistramide A with G-actin but not required for actin-severing activity. Thus, removal of the highly reactivity enone-containing subunit C was expected to provide access to a simplified congener that could reversibly interact with the actin cytoskeleton and inhibit tumor growth in vitro and in vivo but would not have the general toxicity observed in the case of bistramide A. While we previously demonstrated that structural simplifications of the bistramide framework were possible, such modifications typically decreased actin-binding and the actin-severing activity of the resulting analogs, in some cases substantially. Retention of the fully elaborated spiroketal subunit A, as well as the intact central amide fragment B was expected to preserve the majority of the hydrophobic and polar interactions with actin, which would in turn maximize the potency of this compound.

Based on this hypothesis, we designed and synthesized analog 10 (Scheme 12). The synthesis began with alcohol 42, which has been described previously. Swern oxidation of 42 followed by Horner-Wadsworth-Emmons olefination of the resulting aldehyde with the phosphonate 54 gave 55. Itsuno-

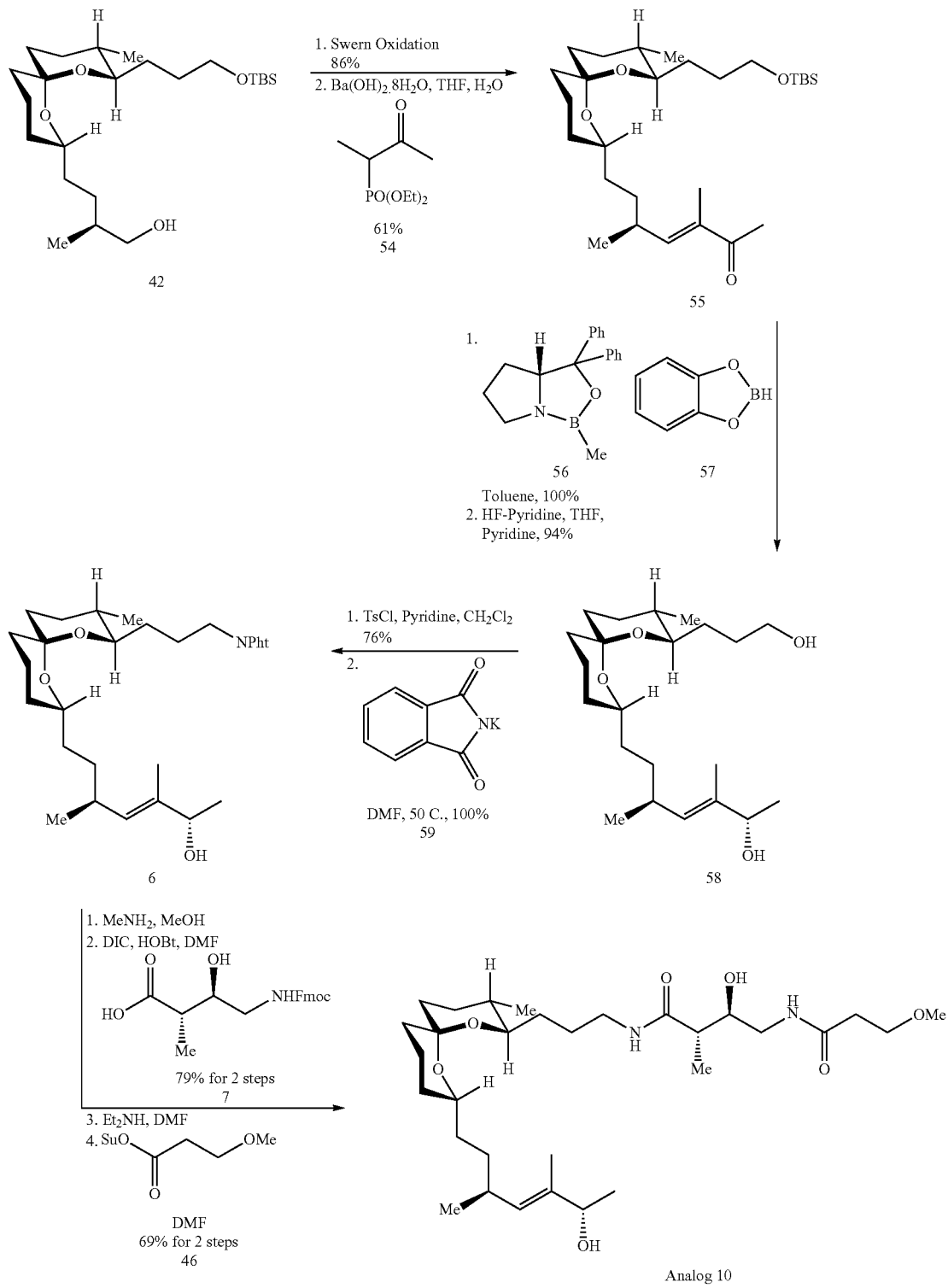

Corey reduction and removal of the TBS group gave alcohol 58. Conversion of this alcohol into the corresponding tosylate, followed by displacement with phthalimide afforded fully functionalized spiroketal-containing fragment 6. Final three-step coupling protocol enabled efficient production of the desired target 10 on 100 mg scale.

Isothermal titration calorimetry established the dissociation constant ($K_d$) value of 9.0 nM for binding of 10 to G-actin, which was comparable to that of the parent natural product ($K_d$=7.0 nM) and proved superior to other synthetic bistramide derivatives. The high actin-binding affinity of 10 was attributed to the van der Waals interactions between several lipohilic amino acid side chains of actin and a fully extended C(31)-C(38) terminus of the spiroketal-bearing subunit A. This result further confirmed that pyran-containing fragment C did not significantly contribute to the actin-binding affinity of bistramide-based agents.

Encouraged by the initially observed potent G-actin binding affinity of 10, we next employed time-lapse total internal reflection fluorescence (TIRF) microscopy to examine the effects of this compound on depolymerization of filamentous actin in vitro. We initially assembled individual actin filaments by elongating them from a pool of 1.0 µM Mg-ATP-actin monomers supplemented with a trace of 0.5 µM Mg-ATP-actin monomers labeled with Oregon green for visualization. The resulting filaments were incubated with either a solution of buffer or a 1.5 µM solution of 10 and imaged with TIRF microscopy. As expected, addition of buffer did not substantially impact the stability of actin filaments. On the other hand, treatment of F-actin with 10 resulted in rapid filament disassembly. Similar to our previous observations, the mechanism of actin depolymerization by 10 entailed formation of multiple filaments breaks, which in turn created subsequent points for actin disassembly.

We also examined the ability of 10 to depolymerize F-actin in live cells. The actin cytoskeleton can be readily visualized by fluorescent microscopy following Alexa Fluor 488 phalloidin staining. This experiment revealed that 10 depolymerized F-actin in A549 cells in a dose-dependent manner. Importantly, noticeable actin disassembly was detected even at 250 nM of 10, which further verified potency of this agent now at the cellular level. A similar effect of 10 on F-actin depolymerization was also observed in a DU145 prostate cancer cell line.

We examined the effect of 10 on growth in PC3 and A549 cell lines 24, 48, 72 and 96 h after incubation of the cells with the drug. Analog 10 efficiently inhibited the growth of A549 cells in a dose-dependent manner. Complete growth inhibition was observed at concentrations as low as 5 µM. Interestingly, PC3 cells were found to be substantially less sensitive to 10 under the same growth conditions. This study revealed highly efficient, dose-dependent growth inhibition. Indeed, the growth of this non-small cell lung cancer cell line was inhibited by 70% at 0.65 mM of 10 and by 85% at 2.5 mM of 10. Similar growth inhibitory effects of 10 were observed on several other cancer cell lines.

Since analog 10 appeared to be significantly more effective in inhibiting growth of A549 cells in vitro, we decided to examine the ability of this compound to inhibit growth of this non-small cell lung carcinoma in vivo. Initially, we established that 10 had no observed toxicity in mice up to 50 mg/kg a single dose administered i.p. Toxicity was assessed by daily weight measurements and mouse behavior compared to non-injected mice. Next, we established tumor xenografts by injecting A549 cells subcutaneously into two groups of nude athymic mice (6 animals per group). The first group was injected only with DMSO control. The second group of animals received three i.p. doses of analog 10 (20 mg/kg) on the $3^{rd}$, $5^{th}$ and $7^{th}$ day after the initial tumor challenge. Tumor growth was monitored over a period of five weeks. The tumor grew rapidly in the control mice population and reached an average size of 731 $mm^3$ at the end of 4 weeks. Tumor growth was substantially inhibited by analog 10. The average tumor size for this population was 308 $mm^3$ after 4 weeks. The significance of this result is two-fold. First, administration of the drug only during the first week following initial tumor challenge had a long-lasting effect on growth of rapidly proliferating tumors. Second, no significant drug-based cytotoxicity was observed at this concentration.

Our results demonstrate that the two factors that contribute to the highly potent cytotoxic activity of bistramide A are the severing of filamentous actin and the sequestration of monomeric actin. Without wishing to be bound by theory, we believe that covalent G-actin sequestration, which is expected to further promote F-actin depolymerization, plays a role in increasing the cytotoxicity of bistramide A and the C(1)-C(4) enone containing analogs 2 and 3. Indeed, analog 3 is more cytotoxic and depolymerizes actin in cells much more effectively than analog 4, whereas the in vitro filament-severing abilities and actin-binding affinities of the two compounds are the opposite. This result could be explained by covalent sequestration of monomeric actin by enone-containing analog 3, which would lead to (i) depletion of the pool of monomeric actin in the cell and subsequent actin depolymerization; and (ii) more efficient delivery of analog 3 into the cell due to the irreversible shift in chemical equilibrium after formation of the covalent actin-small molecule complex. In the absence of the C(1)-C(4) enone, analogs 4 and 5 are expected to be much less effective at sequestering monomeric actin due to reversible G-actin binding and competition with a range of other actin-binding proteins in the cell. Our results explain the reported differences in the abilities of bistramides A, D and K to inhibit tumor growth in the carcinoma mouse xenograft model. Bistramide A was ineffective at reducing tumor growth due to the high general toxicity of this compound. The toxicity of bistramide A can now be explained by facile delivery of this compound into vital organs due to the covalent interaction with its protein target, which is abundant in healthy tissues. On the other hand, bistramides D and K, which are devoid of the C(1)-C(3) enone, were found to be effective at inhibiting tumor growth in vivo with no observed toxicity of bistramide K up to 200 mg/kg (20). Due to the inability to covalently modify actin in the absence of the enone moiety, bistramides D and K are significantly less toxic to normal cells. The efficacy of these compounds can be explained by the severing of actin filaments, even in the absence of C(1)-C(3) enone moiety, which would result in inhibition of the proliferation of rapidly dividing tumor cells. Indeed, our initial in vitro and in vivo studies using a rationally designed bistramide analog 10, which was devoid of the enone moiety, validated earlier in vivo observations.

Throughout this description and in the appended claims, the following definitions are to be understood:

The term "alkyl" refers to a substituted or unsubstituted, straight, branched or cyclic hydrocarbon chain containing, preferably, from 1 to 20 carbon atoms. Representative examples of unsubstituted alkyl groups for use in accordance with the present invention include but are not limited to methyl, ethyl, propyl, iso-propyl, cyclopropyl, butyl, iso-butyl, tert-butyl, sec-butyl, cyclobutyl, pentyl, cyclopentyl, hexyl, cyclohexyl, and the like.

The term "alkenyl" refers to a substituted or unsubstituted, straight, branched or cyclic, unsaturated hydrocarbon chain that contains at least one double bond and, preferably, from 2 to 20 carbon atoms. Representative unsubstituted alkenyl groups for use in accordance with the present invention include but are not limited to ethenyl or vinyl (—CH=CH$_2$), 1-propenyl, 2-propenyl or allyl (—CH$_2$—CH=CH$_2$), 1,3-butadienyl (—CH=CHCH=CH$_2$), 1-butenyl(—CH=CHCH$_2$CH$_3$), hexenyl, pentenyl, 1,3,5-hexatrienyl, and the like. Preferred cycloalkenyl groups are those having from five to eight carbon atoms and at least one double bond. Representative cycloalkenyl groups for use in accordance with the present invention include but are not limited to cyclohexadienyl, cyclohexenyl, cyclopentenyl, cycloheptenyl, cyclooctenyl, cyclohexadienyl, cycloheptadienyl, cyclooctatrienyl, and the like.

The term "alkoxy" refers to a substituted or unsubstituted —O-Alkyl group. Representative unsubstituted alkoxy groups for use in accordance with the present invention include but are not limited to methoxy, ethoxy, n-propoxy, iso-propoxy, n-butoxy, t-butoxy, and the like.

The terms "siloxy" and "silyloxy" refer to silicon substituted oxygen groups. The silicon-containing portion of the siloxy group may be substituted or unsubstituted. Representative siloxy groups for use in accordance with the present invention include but are not limited to trimethylsilyloxy (—OSi(CH$_3$)$_3$), triethylsilyloxy (—OSi(CH$_2$CH$_3$)$_3$), triisopropylsiloxy (—OSi(i-Pr)$_3$), t-butyldimethylsilyloxy (—OSi(t-Bu)(CH$_3$)$_2$), and the like.

The term "alkynyl" refers to a substituted or unsubstituted, straight, branched or cyclic unsaturated hydrocarbon chain containing at least one triple bond and, preferably, from 2 to 20 carbon atoms.

The term "amino" refers to an unsubstituted or substituted amino (—NH$_2$) group. The amine may be primary (—NH$_2$), secondary (—NHR$^a$) or tertiary (—NR$^a$R$^b$, wherein R$^a$ and R$^b$ are the same or different). Representative substituted amino groups for use in accordance with the present invention include but are not limited to methylamino, dimethylamino, ethylamino, diethylamino, 2-propylamino, 1-propylamino, di(n-propyl)amino, di(iso-propyl)amino, methyl-n-propylamino, t-butylamino, and the like.

The term "halogen" refers to fluorine, chlorine, iodine or bromine.

The term "heterocyclic" refers to a saturated, partially unsaturated, or aromatic ring system containing from 3 to 20, preferably 4 to 8, carbon atoms, and at least one, preferably 1 to 3, heteroatoms. The ring may optionally be substituted with one or more substituents. Moreover, the ring may be mono-, bi- or polycyclic. Preferred heteroatoms for inclusion in the ring include but are not limited to nitrogen, oxygen, and sulfur. Representative heterocyclic groups for use in accordance with the present invention include but are not limited to acridine, benzathiazoline, benzimidazole, benzofuran, benzothiapene, benzthiazole, benzothiophenyl, carbazole, cinnoline, furan, imidazole, 1H-indazole, indole, isoindole, isoquinoline, isothiazole, morpholine, oxazole (e.g., 1,2,3-oxadiazole), phenazine, phenothiazine, phenoxazine, phthalazine, piperazine, pteridine, purine, pyrazine, pyrazole, pyridazine, pyridine, pyrimidine, pyrrole, quinazoline, quinoline, quinoxaline, thiazole, 1,3,4-thiadiazole, thiophene, 1,3,5-triazines, triazole (e.g., 1,2,3-triazole), and the like.

The term "substituted" refers to the optional attachment of one or more substituents onto a backbone structure (e.g., an alkyl group, an alkenyl group, etc.). Representative substituents for use in accordance with the present invention include but are not limited to hydroxyl, amino (—NH$_2$, —NHR$^a$, —NR$^a$,R$^b$), oxy (—O—), carbonyl (—CO—), thiol, alkyl, alkenyl, alkynyl, alkoxy, halo, nitrile, nitro, aryl and heterocyclyl groups. These substituents can optionally be further substituted with 1 to 3 substituents. Examples of substituted substituents include carboxamide, alkylmercapto, alkylsulphonyl, alkylamino, dialkylamino, carboxylate, alkoxycarbonyl, alkylaryl, aralkyl, alkylheterocyclyl, heterocyclylaryl, haloalkyl, and the like. When necessary, protecting groups may used to protect functional substituents, as is well known in the art (see: Protective Groups in Organic Synthesis, 3$^{rd}$ Edition by Theodora W. Greene and Peter G. M. Wuts, John Wiley & Sons, Inc., New York, 1999).

EXPERIMENTAL SECTION

General

Methanol (HPLC grade), toluene (HPLC grade), ethyl acetate (ACS grade, and HPLC grade), hexane (ACS grade and HPLC grade), acetonitrile (HPLC grade), chloroform (HPLC grade), diethyl ether (ACS grade), benzene (ACS grade) were purchased from Fisher Scientific and used without further purification. DMSO (anhydrous grade), DMF (anhydrous grade) were purchased from ACROS. Alexa Fluor 488 Phalloidin and BODIPY 650-665 SE was purchased from Invitrogen. Dichloromethane and tetrahydrofuran was purified by distillation. Commercially available reagents were used without further purification. Reactions were monitored by thin layer chromatography (TLC) using Whatman precoated silica gel plates. Flash column chromatography was performed over ultra pure silica gel (230-400 mesh) from Silicycle. $^1$H NMR and $^{13}$C NMR spectra were recorded on Bruker DMX-500 and Bruker DMX-400 spectrometers using residual solvent peaks as an internal standard. Mass Spectra were recorded with Agilent 1100 LCMS; APCI or API-ES, POS, SCAN, 70. Actin was purified from rabbit muscle acetone powder (Pel-FreezBiologicals) by the method of reported by Pardee and Spudich and its purity ascertained by SDS-PAGE. It was stored by flash freezing in liquid nitrogen as a solution in G-buffer [2 mM TRIS-base (Fisher) pH 8.0, 0.2 mM CaCl$_2$ (Fisher), 0.2 mM ATP (Calbiochem), 0.01% NaN$_3$ (Sigma), 0.2 mM β-mercaptoethanol (Sigma)]. TMR-actin and biotin-actin were prepared by reported methods. Natural bistramide A was provided by Professor G. F. Biard (University of Nantes). Necessary x-ray crystallography equipment and TCEP was purchased from Hampton Research. PEG 1500 was purchased from Fluka. MES was purchased from Sigma. iProof polymerase was purchased from Bio-Rad Laboratories. BL21-Codon plus (DE3)-RP cells were purchased from Stratagene. Talon Metal Affinity resin was purchased from Clontech. The Hi-TRAP Q and Mono Q FPLC columns were purchased from GE Healthcare. Antifoam 204 was purchased from Sigma.

X-Ray Crystallography

Crystallization. Crystals of the bistramide A-actin complex were grown by the hanging drop method. Bistramide A was mixed with actin in a 1:1 ratio, filtered and concentrated by ultrafiltration (Millipore Ultrafree-0.5) to ca. 10 mg/ml. The bistramide A-actin complex solution (2 μL) was mixed with 2

μL of crystallization buffer [100 mM MES pH 6.0, 24% (w/v) PEG 1500, 70 mM CaCl₂, 1 mM NaN₃, 1 mM TCEP and the hanging drop was equilibrated at 19° C. over 1 ml crystallization buffer. Rectangular crystals appeared in one week. For low temperature data collection, crystals were transferred to the cryoprotectant (crystallization buffer plus 20% (w/v) sucrose) for a few seconds and flash-frozen in liquid nitrogen.

Data Collection. X-Ray data were collected at 100 K using 1,0000 Å wavelength at Southeast Regional Collaborative Access Team (SER-CAT) 22-ID beam line at the Advanced Photon Source, Argonne National Laboratory. Supporting institutions may be found at www.ser-cat.org/members.html. Total of 360 frames (0.5° oscillation width) were collected using the crystal-to-detector distance 175 mm. The exposure time was 3 sec per frame.

Data Processing, Refinement And Analysis Of Data. X-ray data were processed and scaled in HKL2000. The structure was solved by molecular replacement using MOLREP and 1J6Z structure containing uncomplexed actin as a starting model. The rigid body refinement, simulated annealing and the search for water molecules were carried out with CNS1.1. The Sigma A-weighted $2F_{obs}-F_{calc}$ and $F_{obs}-F_{calc}$ Fourier maps were calculated using CCP4. The Fourier maps were displayed and examined in TURBO-FRODO. The bistramide A model was built and four $Ca^{+2}$ sites as well as ATP molecule were added in at this stage. The TLS (Translation/Libration/Screw) and bulk solvent parameters, restrained temperature factor, and final positional refinement were completed with REFMAC5. R-free was monitored by setting aside 5% of the reflection as a test set. The hydrogen atoms were included in the refinement in the riding positions. A Ramachandran plot calculated with PROCHECK indicates that 100% of the non-Gly and non-Pro residues in the final models lie in the most favored and additional allowed regions. 361 amino acids (residues 4-43, 51-371) are well defined in the electron density maps. The bistramide A-actin contacts were identified using PYMOL. Figures showing the electron density map and three-dimensional structures were prepared using TURBO-FRODO and PYMOL.

TABLE 3

Data collection and refinement statistics

| | Bistramide A-actin complex |
|---|---|
| Data Collection[a] | |
| Space Group | C2 |
| Unit cell dimensions | |
| a (Å) | 60.13 |
| b (Å) | 56.51 |
| c (Å) | 101.65 |
| α (°) | 90.0 |
| β (°) | 94.6 |
| γ (°) | 90.0 |
| Resolution (Å)[b] | 50-1.35 (1.45-140, 1.40-1.35) |
| Average I/σ[b] | 27.6 (4.2, 2.6) |
| Completeness (%)[b] | 97.5 (95.3, 81.4) |
| $R_{merge}$[b] | 0.046 (0.296, 0.389) |
| Redundancy[b] | 3.5 (2.9, 2.2) |
| Refinement | |
| Unique reflections[b] | 62867 (6845, 6061) |
| $R_{work}$[b] (%) | 17.4 (21.0, 25.8) |
| $R_{free}$[b] (%) | 20.1 (25.0, 28.1) |
| No. of atoms | |
| Actin | 2838 |
| Bistramide A | 50 (4 are disordered) |
| ATP | 31 |

TABLE 3-continued

Data collection and refinement statistics

| | Bistramide A-actin complex |
|---|---|
| $Ca^{2+}$ ions/water | 4/416 |
| Wilson B-value (Å²) | 24.3 |
| B-factors (Å²) | |
| Actin | 21.7 |
| Bistramide A | 22.8 |
| ATP | 16.6 |
| $Ca^{2+}$ ions/water | 21.4/30.6 |
| R.m.s. deviation | |
| Bond length (Å) | 0.016 |
| Bond angles (°) | 1.61 |

[a]One crystal was used for data collection
[b]Data in parentheses correspond to two last resolution shells.

Synthesis of Analogs

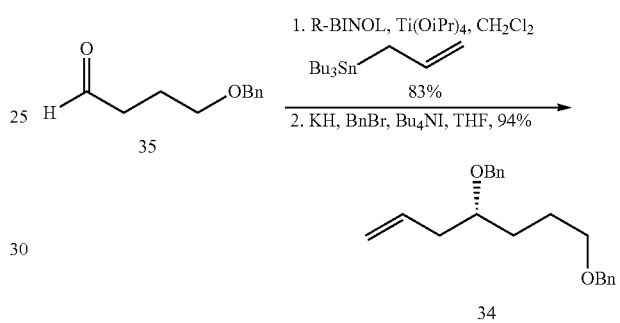

A solution of R-BINOL (1.02 g, 3.58 mmol) in CH₂Cl₂ (30 ml) was treated with 3 Å molecular sieves (6.0 g) and Ti(O-iPr)₄ (1.06 ml, 3.58 mmol) and refluxed for 1 h. The resulting mixture was cooled to 20° C., treated with 4-benzyloxybutyraldehyde 35 (3.19 g, 17.9 mmol) in 10 ml CH₂Cl₂, cooled further to −78° C. and treated with allyltributylstannane (6.66 ml, 21.5 mmol). The reaction mixture was stirred for 3 days at −20° C., treated with saturated aqueous solution of Na₂CO₃ (50 ml) and CH₂Cl₂ (50 ml). The stirring continued for 2 h. The reaction mixture was filtered. The layers were separated. The aqueous layer was extracted with CH₂Cl₂ (2×50 ml). Combined organic layers were dried with MgSO₄, filtered and concentrated. The product was purified by flash column chromatography on silica gel (elution with 4:1 hexane:EtOAc) followed by bulb-to-bulb distillation to give the expected alcohol (2.51 g, 83% yield) in 91% ee (Mosher ester analysis). A portion of this compound (1.10 g, 5 mmol) was dissolved in THF (20 ml) at 0° C. and treated with KH (300 mg, 7.5 mmol), benzyl bromide (1.03 g, 6 mmol) and Bu₄NI (100 mg, 0.27 mmol). The reaction was quenched with saturated aqueous solution of NH₄Cl (20 ml) and CH₂Cl₂ (20 ml). The layers were separated. The aqueous layer was extracted with CH₂Cl₂ (3×20 ml). Combined organic layers were dried with MgSO₄, filtered and concentrated. Purification by flash column chromatography on silica gel (elution with 5:1 hexane:EtOAc) gave alkene 34 (1.47 g, 94% yield). ¹H NMR (400 MHz, CDCl₃) δ 1.68-1.97 (m, 4H), 2.46 (m, 2H), 3.54-3.62 (m, 3H), 4.56-4.71 (m, 4H), 5.16-5.27 (m, 2H), 5.98 (m, 1H), 7.33-7.49 (m, 10H); ¹³C NMR (125 MHz, CDCl₃) δ 25.7, 30.4, 38.3, 70.4, 70.9, 72.8, 78.2, 117.1, 127.5, 127.5, 127.6, 127.8, 128.2, 128.3, 128.4, 134.9, 138.7, 138.9; MS calculated for $O_{21}H_{26}O_2$ 310.19 $(M)^+$, found 311.2 $(M+H)^+$.

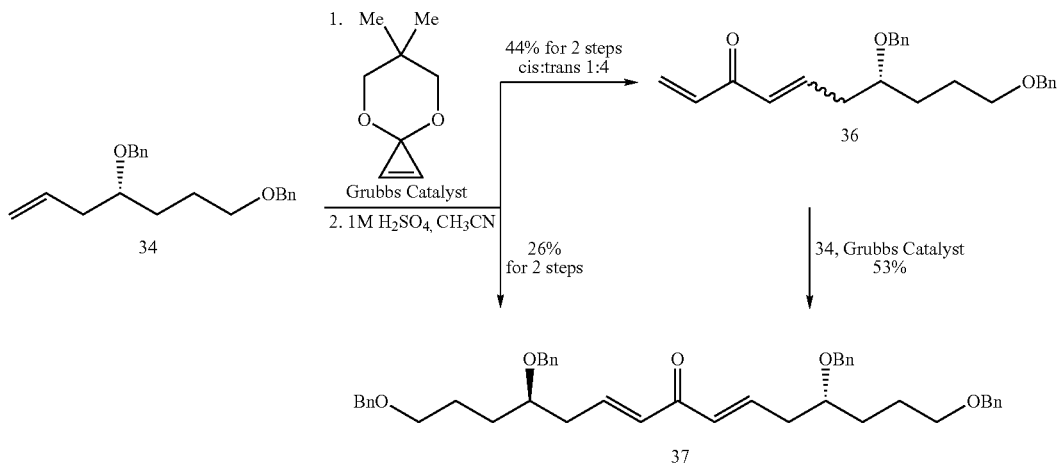

Enone 37. Alkene 34 (1.0 g, 3.22 mmol) was dissolved in benzene (25 ml) and treated with cyclopropenone acetal (452 mg, 3.22 mmol) and Grubbs catalyst II (274 mg, 0.32 mmol). The reaction mixture was stirred at 60° C. for 1.5 h, concentrated and purified by column chromatography (elution with 10:1-5:1 hexane:EtOAc) to give a mixture of products, which was dissolved in $CH_3CN$ (25 ml) and treated with 1M aqueous $H_2SO_4$ (0.1 ml). Upon completion of the reaction, water (25 ml) was added and the product was extracted in ether (2×25 ml). Combined organic layers were dried with $MgSO_4$, filtered and concentrated. Column chromatography on silica gel (elution with 5:1 Hexane:EtOAc) gave dienone 36 (517 mg, 44% yield for 2 steps, cis:trans 1:4) and dienone 37 (276 mg, 26% for 2 steps, only trans isomer).

A solution of dienone 36 (517 mg, 1.42 mmol) in $CH_2Cl_2$ (20 ml) was treated with alkene 34 (616 mg, 1.98 mmol) and Grubbs catalyst II (120 mg, 0.14 mmol). The reaction mixture was heated to reflux for 6 h, concentrated and purified by flash column chromatography over silica gel (elution with 3:1 hexane:EtOAc) to give more dienone 37 (490 mg, 53% yield, only trans isomer). $^1H$ NMR (400 MHz, $CDCl_3$) δ 1.60-1.82 (m, 8H), 2.49 (t, 4H, J=5 Hz), 3.46 (m, 4H), 3.56 (m, 2H, J=4 Hz), 4.49 (s, 4H), 4.52 (q, 4H, J=9 Hz), 6.37 (d, 2H, J=13 Hz), 6.91 (dt, 2H, J=12, 6 Hz), 7.25-7.36 (m, 20H); $^{13}C$ NMR (125 MHz, $CDCl_3$) δ 25.6, 30.3, 30.8, 37.2, 70.1, 71.1, 72.8, 77.5, 127.5, 127.6, 127.7, 128.3, 128.3, 130.6, 138.3, 138.4, 143.9, 188.8; MS calculated for $C_{43}H_{50}O_5$ 647.37 (M)+, found 647.3 (M+H)+.

Diol 33. A sealed tube was charged with dienone 37 (1.02 g, 1.57 mmol), $Pd(OH)_2$/C (1.1 g, 20 wt %, 1.57 mmol), EtOAc (25 ml), MeOH (25 ml) and pressurized with $H_2$ to 35 psi. After 4.5 h, the reaction mixture was filtered, concentrated and purified by flash column chromatography over silica gel (elution with 1:10 MeOH:EtOAc) to give diol 33 (415 mg, 97% yield). $^1H$ NMR (500 MHz, $CDCl_3$) δ 1.17-1.27 (m, 2H), 1.38 (td, 2H, J=14, 5 Hz), 1.50-1.67 (m, 12H), 1.77 (m, 2H), 1.83 (m, 2H), 2.37 (t, 2H, J=4 Hz), 3.57 (m, 2H), 3.63 (t, 4H, J=6 Hz); $^{13}C$ NMR (125 MHz, $CDCl_3$) δ 18.8, 29.1, 31.1, 32.8, 35.5, 63.1, 69.3, 96.4; MS calculated for $C_{15}H_{28}O_3$ 272.20 (M)−, found 307.17 (M+Cl)−.

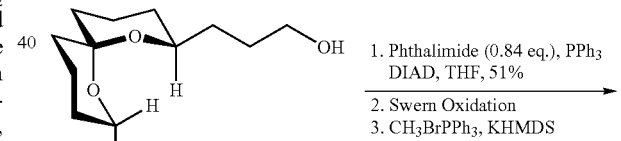

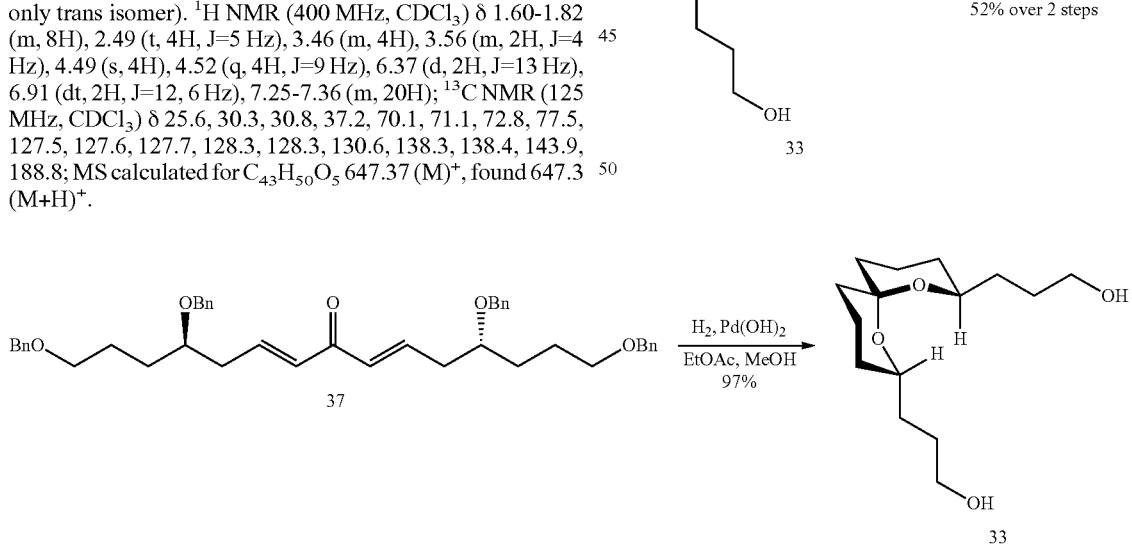

-continued

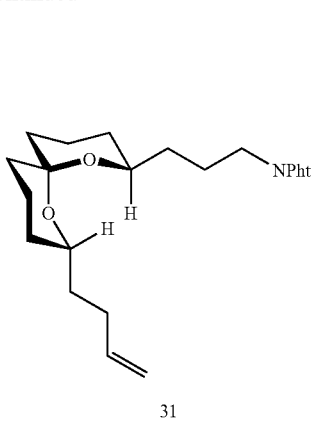

31

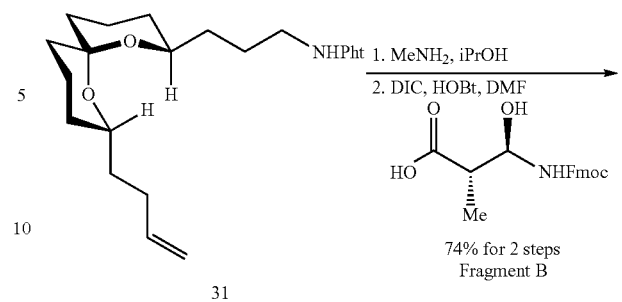

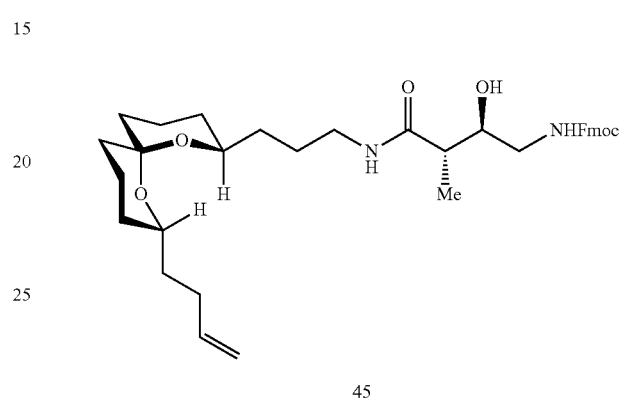

45

Alkene 31. A solution of diol 33 (423 mg, 1.55 mmol) in THF (35 ml) was treated with phthalimide (192 mg, 1.3 mmol), PPh₃ (325 mg, 1.24 mmol) and DIAD (0.24 mL, 1.24 mmol). The reaction mixture was stirred at 20° C. overnight, concentrated and purified by column chromatography on silica gel (elution with 2:1 Et₂O/Hexane) to give the expected N-alkyl phthalimide (0.315 g, 51% yield), which next subjected to Swern oxidation by initial treatment of oxalyl chloride (0.59 mL of 2.0 M in CH₂Cl₂, 1.18 mmol) in CH₂Cl₂ (10 ml) at −78° C. with DMSO (0.17 mL, 2.35 mmol) in CH₂Cl₂ (1 mL). After 5 min, the resulting Swern reagent was treated with alcohol prepared in the previous step (0.315 g, 0.785 mmol). After 45 min, triethylamine (0.66 mL, 4.7 mmol) was added. The reaction was allowed to reach 20° C. and treated with water (10 mL). The organic layer was washed sequentially with saturated aqueous solution of NaCl (10 mL), 1.2 M HCl (10 mL), saturated aqueous solution of NaHCO₃ (10 mL), and H₂O (10 mL), dried with MgSO₄ and concentrated. The resulting aldehyde was next treated with the ylide, which was prepared from CH₃BrPPh₃ (0.214 g, 0.60 mmol) in toluene (10 ml) and KHMDS (1.2 mL, 0.5 M in tol, 0.60 mmol). After 1 h, the reaction was quenched with aqueous solution of NH₄Cl. The layers were separated and the aqueous layer was extracted with Et₂O (2×10 mL). The combined organic layers were dried with Na₂SO₄, concentrated and purified by flash column chromatography on silica gel (elution with 1:1 Et₂O/Hexane) to give alkene 31 (161 mg, 52% yield). $^1$H NMR (500 MHz, CDCl₃) δ 1.15-1.18 (m, 2H), 1.30-1.41 (m, 2H), 1.41-1.60 (m, 10H), 1.63-1.72 (m, 1H), 1.84-1.93 (m, 3H), 2.06-2.11 (m, 1H), 2.25-2.29 (m, 1H), 3.54-3.57 (m, 2H), 3.69-3.81 (m, 2H), 4.90 (m, 1H), 5.01 (m, 1H), 5.80-5.88 (m, 1H), 7.71 (dd, 2H, J=5, 3 Hz), 7.84 (dd, 2H, J=5, 3); $^{13}$C NMR (125 MHz, CDCl₃); δ 18.8, 25.3, 30.1, 31.4, 33.7, 35.6, 38.3, 68.5, 68.6, 95.8, 114.3, 123.2, 132.2, 133.8, 139.0, 168.4; MS calculated for C₂₄H₃₁NO₄ 397.23 (M)$^+$, found 398.1 (M+H)$^+$.

Amide 45. A solution of alkene 31 (161 mg, 0.405 mmol) in i-PrOH (5 ml) was treated with MeNH₂ (2 ml, 40 wt % in H₂O) at room temperature overnight. The resulting solution was concentrated. The residue was partitioned between 1.2 M HCl (5 ml) and Et₂O (5 ml). The aqueous layer was neutralized with 2 M NaOH to pH 7, extracted with EtOAc (5×20 mL) and concentrated to give the primary amine. A portion of this compound (63 mg, 0.239 mmol) was treated with a solution of fragment B (87 mg, 0.245 mmol) in DMF (3 ml), DIC (0.041 mL, 0.263 mmol), and HOBt (34 mg, 0.252 mmol). After 12 h, the reaction mixture was concentrated and purified by flash column chromatography on silica gel (elution with 100% EtOAc) to give amide 45 (107 mg, 74% yield). $^1$H NMR (400 MHz, CDCl₃) δ 1.14-1.19 (m, 2H), 1.27 (d, 3H, J=7 Hz), 1.35-1.58 (m, 13H), 1.62-1.92 (m, 3H), 2.02-2.11 (m, 1H), 2.27-2.29 (m, 2H), 3.15 (dq, 1H, J=6, 5 Hz), 3.26 (t, 1H, J=6 Hz), 3.28 (t, 1H, J=6 Hz), 3.42 (ddd, 1H, J=13, 7, 4 Hz), 3.48-3.50 (m, 2H), 3.64-3.67 (m, 1H), 4.21 (t, 1H, J=6 Hz), 4.37-4.43 (m, 2H), 4.96-5.03 (m, 2H), 5.30 (br t, 1H, J=5 Hz), 5.78-5.88 (m, 1H), 6.25 (m, 1H), 7.30 (t, 2H, J=7 Hz), 7.40 (t, 2H, J=7 Hz), 7.59 (d, 2H, J=7 Hz), 7.76 (d, 2H, J=7 Hz); $^{13}$C NMR (100 MHz, CDCl₃) δ 15.7, 18.7, 18.9, 23.3, 25.7, 30.1, 31.3, 33.5, 35.4, 35.5, 39.5, 42.7, 45.2, 47.2, 66.7, 68.5, 68.8, 73.5, 95.9, 106.4, 114.4, 120.0, 125.0, 127.0, 127.7, 138.9, 141.3, 143.8, 156.9, 175.5; MS calculated for C₃₆H₄₈N₂O₆ (M)$^+$ 604.36, found 605.3 (M+H)$^+$.

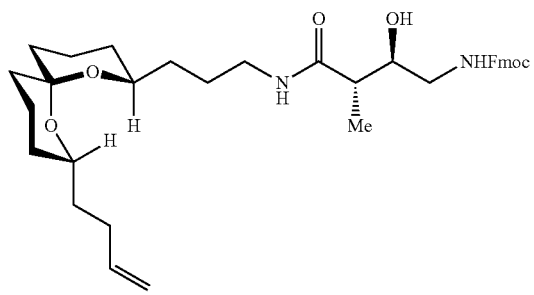
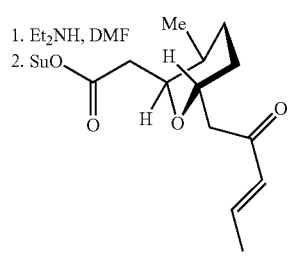

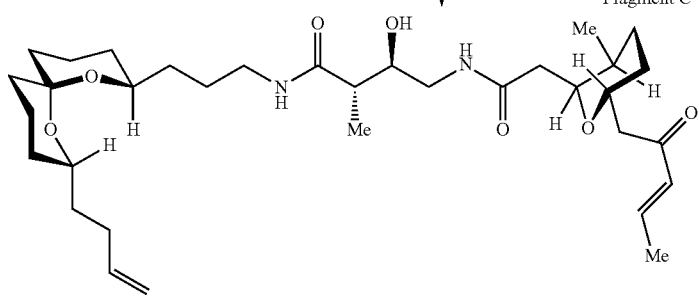

Analog 3

Analog 3. A solution of amide 45 (8 mg, 0.013 mmol) in DMF (1 ml) was treated with Et$_2$NH (0.25 mL, 2.4 mmol). The reaction was stirred for 1 h and concentrated to give primary amine, which was dissolved in DMF (1 ml) and treated with fragment C (5 mg, 0.015 mmol). The reaction was stirred overnight, concentrated and purified by flash column chromatography on silica gel (elution with 9:1 EtOAc/MeOH) to give analog 3 (8 mg, 86% yield). $^1$H NMR (400 MHz, CDCl$_3$) δ 0.85 (d, 3H, J=5 Hz), 1.26 (d, 3H, J=7 Hz), 1.09-1.87 (m, 13H), 1.92 (d, 3H, J=5 Hz), 1.97-2.42 (m, 9H), 2.52 (dt, 1H, J=17, 2 Hz), 2.68-2.77 (m, 2H), 2.90 (dd, 1H, J=17, 9 Hz), 3.21-3.29 (m, 4H), 3.49-3.53 (m, 4H), 3.63-3.66 (m, 1H), 3.72 (t, 1H, J=5 Hz), 4.02-4.06 (m, 1H), 4.21 (t, 1H, J=10 Hz), 4.60 (d, 1H, J=4 Hz), 4.94-5.04 (m, 2H), 5.80-5.94 (m, 1H), 6.12 (dd, 1H, J=15, 1 Hz), 6.85-6.99 (m, 2H), 7.31 (br t, 1H, J=5 Hz); $^{13}$C NMR (100 MHz, CDCl$_3$) δ 15.5, 17.1, 18.5, 18.8, 18.9, 26.0, 26.5, 29.7, 30.1, 30.8, 31.0, 31.3, 31.3, 32.1, 33.3, 35.5, 39.5, 43.3, 44.7, 45.2, 64.7, 68.5, 68.9, 73.8, 74.8, 95.8, 114.4, 132.06, 138.9, 144.6, 172.4, 175.5, 199.1; MS calculated for C$_{34}$H$_{56}$N$_2$O$_7$ (M$^+$) 604.42, found 605.3 (M+H)$^+$.

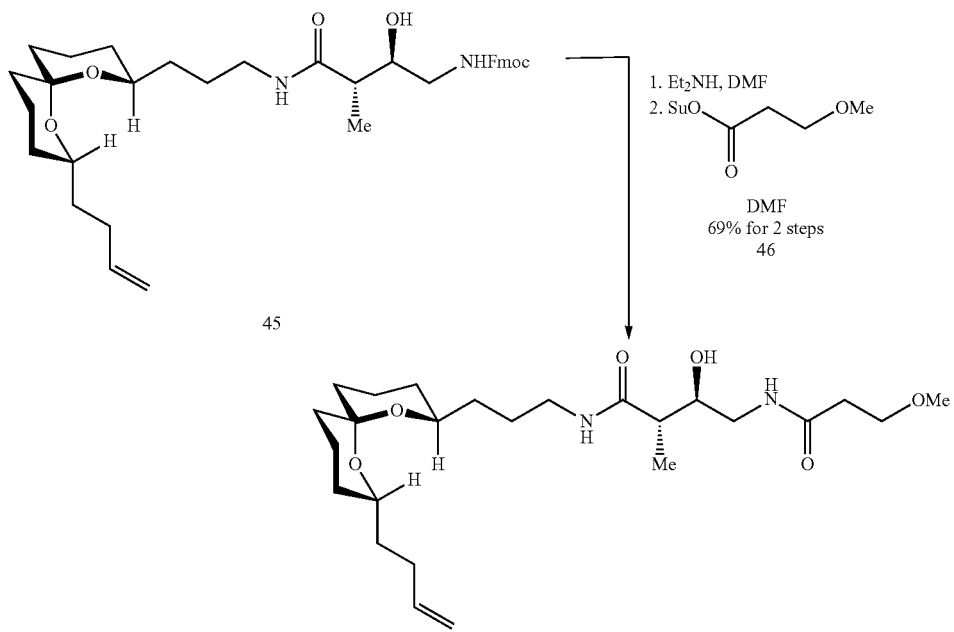

Analog 6

Analog 6. The title compound was prepared in 69% yield according to the procedure, which was used for preparation of analog 3. $^1$H NMR (400 MHz, CDCl$_3$) δ 1.11-1.18 (m, 2H), 1.83 (d, 3H, J=7 Hz), 1.26-1.57 (m, 12H), 1.68-1.92 (m, 3H), 2.04-2.12 (m, 1H), 2.22-2.36 (m, 2H), 2.47 (t, 2H, J=5 Hz), 3.13-3.21 (m, 1H), 3.27 (t, 1H, J=6 Hz), 3.28 (t, 1H, J=6 Hz), 3.37 (s, 3H), 3.50-3.59 (m, 2H), 3.63 (t, 2H, J=6 Hz), 3.64-3.67 (m, 1H), 4.93-5.04 (m, 2H), 5.80-5.84 (m, 1H), 6.42 (br s, 1H), 6.74 (br s, 1H); $^{13}$C NMR (100 MHz, CDCl$_3$) δ 15.6, 18.7, 18.9, 25.7, 30.1, 31.2, 33.5, 35.4, 35.5, 35.6, 36.8, 39.6, 43.0, 44.1, 58.8, 68.5, 68.5, 68.8, 72.5, 73.4, 95.9, 114.4, 138.9, 172.5, 175.7; MS calculated for C$_{25}$H$_{44}$N$_2$O$_6$ (M$^+$) 468.3, found 503.1 (M+Cl)$^-$.

6H), 0.89 (s, 9H), 0.91 (d, 3H, J=14 Hz), 1.11 (d, 3H, J=8 Hz), 1.46-1.81 (m, 8H), 2.48 (t, 2H, J=7 Hz), 2.70 (sextet, 1H, J=7 Hz), 3.28 (m, 2H), 3.40, (q, 1H, J=5 Hz), 3.52 (m, 1H), 3.59 (t, 2H, J=6 Hz), 4.49 (s, 2H), 4.52 (d, 4H), 6.33 (d, 1H, J=16 Hz), 6.40 (d, 1H, J=16 Hz), 6.92 (m, 2H), 7.26-7.4 (m, 15H); $^{13}$C NMR (100 MHz, CDCl$_3$)

δ 4.9, 15.2, 15.2, 17.4, 17.4, 26.2, 27.6, 29.0, 29.4, 29.5, 31.7, 31.8, 33.8, 37.5, 37.7, 40.4, 40.4, 63.3, 71.4, 71.5, 72.2, 73.3, 75.9, 76.0, 78.4, 82.3, 127.7, 127.8, 127.9, 128.1, 128.8, 128.8, 130.8, 138.7, 138.8, 139.0, 144.3, 150.2, 189.4; MS calculated for C$_{45}$H$_{64}$O$_5$Si (M)$^-$=712.45, found 747.3 (M+Cl)$^-$.

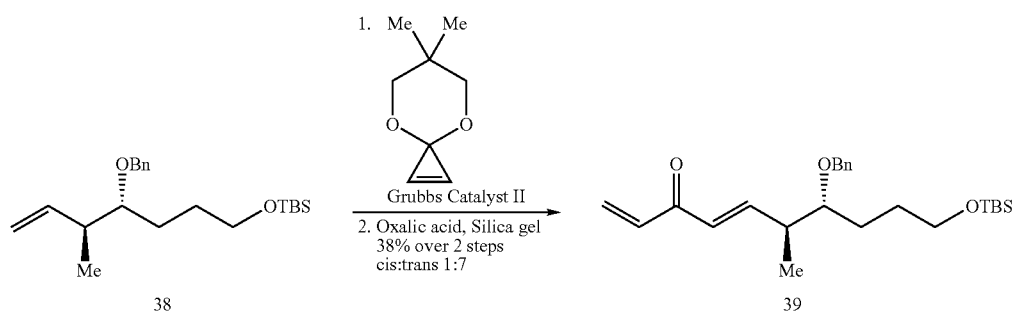

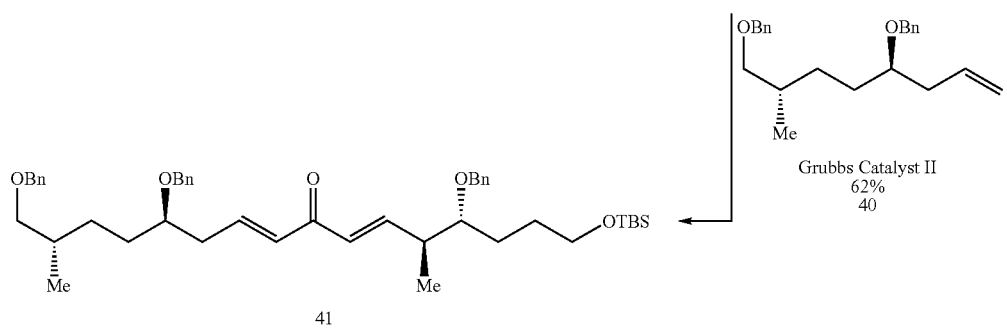

Dienone 13. A solution of known alkene 38 (12.8 g, 36.8 mmol) in benzene (280 ml) was trated with cyclopropenone acetal (7.72 g, 55.2 mmol) and Grubbs catalyst II (3.11 g, 3.68 mmol). The reaction was stirred at 70° C. for 3 h. Solvents were evaporated and the mixture was subjected to purification by column chromatography on silica gel (elution with 20:1 hexane:EtOAc) to give the product of ring-opening metathesis as a mixture of E/Z isomers, which was dissolved in 20 ml of CH$_2$Cl$_2$ and treated for 15 min with a slurry of silica gel (30 g) in CH$_2$Cl$_2$ (75 ml) containing a solution of 10% oxalic acid in water (3 ml). The silica gel was removed by filtration. The filtrate was dried with MgSO$_4$. The solvents were evaporated. The product was purified by column chromatography on silica gel (elution with 15:1 hexane:EtOAc) to give the expected enone 39 (5.65 g, 38% yield, cis:trans 1:7), which was dissolved in CH$_2$Cl$_2$ and treated with known alkene 40 (1.47 g, 4.35 mmol) and Grubbs catalyst II (371 mg, 0.435 mmol) and refluxed for 5 h. The reaction was allowed to stir overnight at room temperature. Solvents were evaporated and the product was purified by column chromatography on silica gel (elution with 10:1-7:1 hexane:EtOAc) to give dienone 41 (1.91 g, 62% yield). $^1$H NMR (400 MHz, CDCl$_3$) δ 0.04 (s,

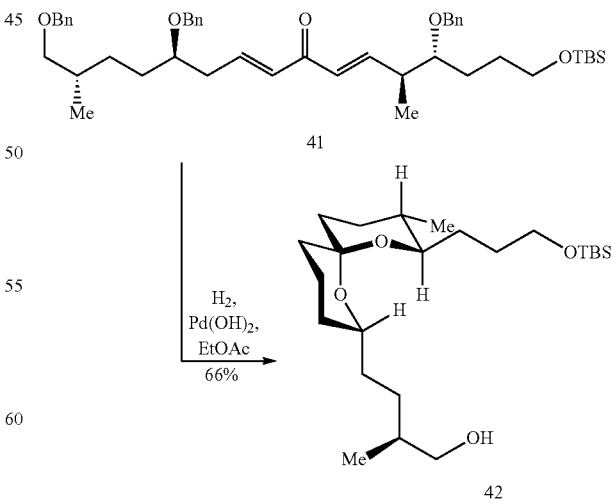

Alcohol 42. A solution of enone 41 (1.91 g, 2.68 mmol) in EtOAc (120 ml) was treated with Pd(OH)$_2$/C (20% wt, 1.90 g). The resulting mixture was stirred under a 1 atm. H$_2$ atmosphere for 2 h and filtered. The product was purified by column chromatography (elution with 100% ethyl acetate) to give alcohol 42 (758 mg, 66% yield). $^1$H NMR (400 MHz, CDCl$_3$) δ 0.05 (s, 6H), 0.81 (d, 3H, J=5 Hz), 0.89 (s, 6H), 0.92 (d, 3H, J=6 Hz), 1.10-1.90 (m, 22H), 3.13 (td, 1H, J=2, 10 Hz), 3.42 (dd, 1H, J=6, 10 Hz), 3.50 (dd, 1H, J=6, 10 Hz), 3.47 (m, 1H), 3.63 (m, 2H); $^{13}$C NMR (100 MHz, CDCl$_3$) δ −5.3, 16.7, 17.9, 18.3, 18.9, 25.9, 27.9, 29.1, 29.2, 29.3, 31.2, 33.5, 35.0, 35.4, 35.7, 35.9, 63.4, 68.0, 69.2, 74.3, 95.4; MS calculated for C$_{28}$H$_{44}$O$_4$Si (M)$^−$ 428.33, found 463.1 (M+Cl)$^−$.

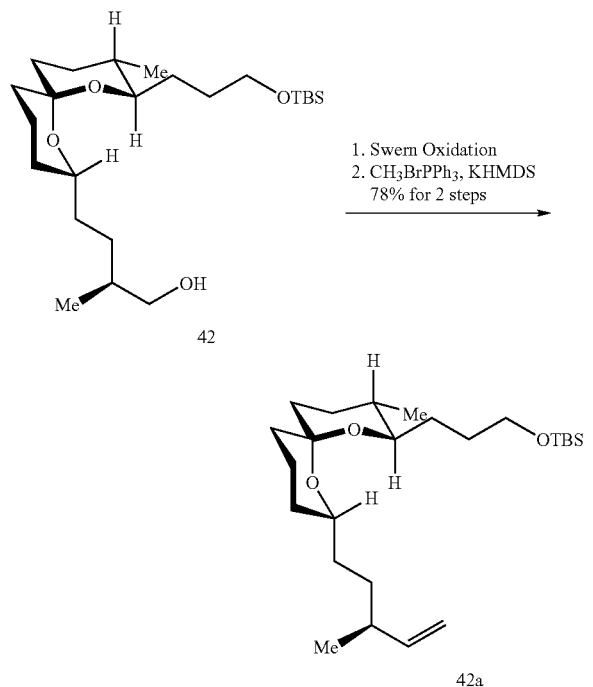

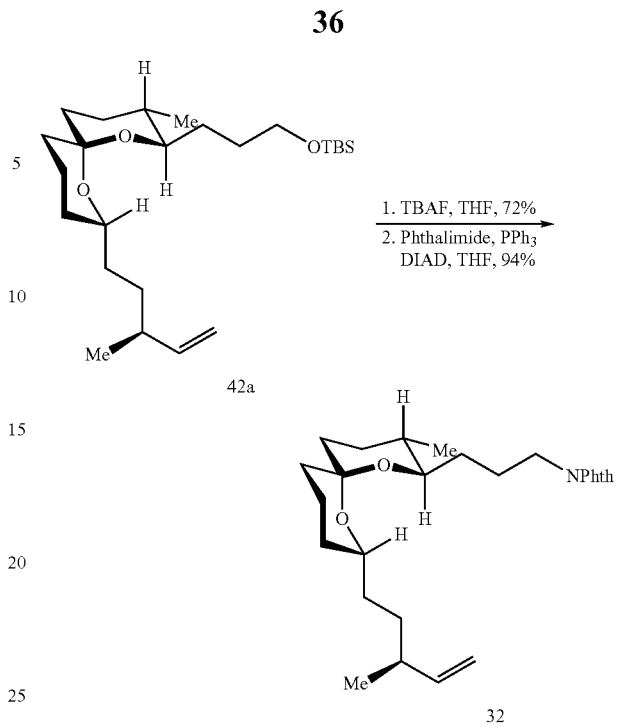

Alkene 42a. A solution of oxalyl chloride (1.2 mL, 13.9 mmol) in CH$_2$Cl$_2$ (100 ml) at −78° C. was treated with DMSO (2.0 mL, 27.6 mmol) in CH$_2$Cl$_2$ (10 ml). The reaction mixture was stirred for 5 min and treated with alcohol 42 (738 mg, 9.3 mmol). After 45 min, triethylamine (7.7 mL, 55.6 mmol) was added. The reaction mixture was warmed to room temperature and treated with water (100 mL). The organic layer was washed sequentially with brine, 1.2 M HCl, saturated NaHCO$_3$, and H$_2$O (100 mL of each solution). The organic layer was dried with MgSO$_4$ and concentrated to give the expected aldehyde, which was treated with a solution of ylide, which was prepared at 0° C. from CH$_3$BrPPh$_3$ (4.06 g, 11.4 mmol) in toluene (80 ml) and KHMDS (22 mL, 0.5 M in toluene, 11.2 mmol). The reaction was quenched with saturated NH$_4$Cl and the aqueous layer was extracted with Et$_2$O (2×100 mL). The combined organic layers were dried with Na$_2$SO$_4$ and concentrated. The residue was purified by column chromatography (elution with 1:1 Et$_2$O/Hexane) to give alkene 42a (605 mg, 78% yield). $^1$H NMR (500 MHz, CDCl$_3$) δ 0.06 (s, 6H), 0.83 (d, 3H, J=6 Hz), 0.90 (s, 9H), 0.99 (d, 3H, J=7 Hz), 1.35-1.91 (m, 19H), 2.13 (apparent sept, 1H, J=7 Hz), 3.14 (td, 1H, J=10, 2 Hz), 3.38-3.44 (m, 1H), 3.51-3.64 (m, 2H), 4.82-4.91 (m, 2H), 5.63 (ddd, 1H, J=17, 10, 7 Hz); $^{13}$C NMR (100 MHz, CDCl$_3$) δ −5.2, 18.0, 19.1, 20.1, 26.0, 28.0, 29.3, 29.4, 31.4, 32.6, 34.0, 35.2, 35.5, 36.1, 37.7, 63.5, 69.0, 74.4, 95.8, 112.5, 144.6; MS calculated for C$_{25}$H$_{48}$O$_3$Si (M)$^+$ 424.35, found 425.2 (M+H)$^+$.

Alkene 32. A solution of alkene 42a (397 mg, 0.95 mmol) was treated with TBAF (1.0 mL of 1.0 M in THF, 1.0 mmol) in 10 mL of THF. The reaction was stirred for 12 h and concentrated. The crude product was purified by column chromatography (elution with 1:1 Et$_2$O/Hex) to give the alcohol (206 mg, 72%), which was dissolved in THF (10 ml) and treated with phthalimide (111 mg, 0.75 mmol), PPh$_3$ (200 mg, 1.24 mmol) and DIAD (0.15 mL, 0.75 mmol). The reaction mixture was stirred at room temperature for 12 h and concentrated. The residue was purified by column chromatography (elution with 2:1 Et$_2$O/Hexane) to give alkene 32 (282 mg, 94% yield). $^1$H NMR (500 MHz, CDCl$_3$) δ 0.81 (d, 3H, J=6 Hz), 0.99 (d, 3H, J=7 Hz), 1.12-1.19 (m, 1H), 1.24-1.74 (m, 16H), 1.84 (qt, 1H, J=13, 4 Hz), 1.95-2.06 (m, 1H), 2.08-2.11 (m, 1H), 3.17 (td, 1H, J=10, 2 Hz), 3.45-3.48 (m, 1H), 3.71-3.75 (m, 2H), 4.88-4.95 (m, 2H), 5.68 (ddd, 1H, J=17, 10, 7 Hz), 7.71 (dd, 2H, J=5, 3 Hz), 7.85 (dd, 2H, J=5, 3 Hz); $^{13}$C NMR (125 MHz, CDCl$_3$) δ 18.1, 19.1, 20.1, 25.3, 27.9, 30.7, 31.4, 32.6, 34.0, 35.1, 35.5, 36.1, 37.7, 38.4, 69.1, 74.1, 95.4, 112.4, 123.2, 132.3, 133.8, 144.8, 168.5; MS calculated for C$_{27}$H$_{37}$NO$_4$ (M)$^+$ 439.28, found 440.2 (M+H)$^+$.

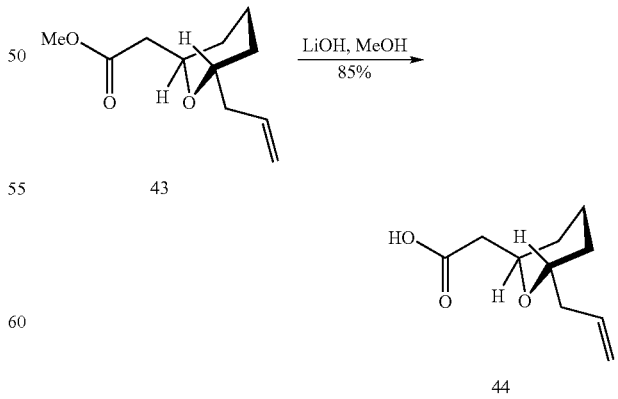

Carboxylic Acid 44. A solution of known ester 43 (129 mg, 0.65 mmol) in MeOH (5 ml) was cooled to 0° C. and treated with a solution of LiOH (5 ml, 0.5 M in water) and stirred for 3 h. The reaction was acidified to pH 2 and extracted in EtOAc (5×10 ml) to give 44 (102 mg, 85% yield). $^1$H NMR (400 MHz, CDCl$_3$) δ 1.40 (m, 2H), 1.57-1.78 (m, 4H), 2.21 (m, 1H), 2.38-2.50 (m, 2H), 2.68 (dd, 1H, J=9, 15 Hz), 3.85 (m, 1H), 4.21 (m, 1H), 5.02-5.10 (m, 2H), 5.77 (m, 1H); $^{13}$C NMR (100 MHz, CDCl$_3$) δ 18.1, 28.7, 29.7, 37.4, 39.0, 67.7, 71.7, 117.0, 134.7, 176.2; MS calculated for C$_{10}$O$_{16}$O$_3$ (M)$^+$ 184.11, found 207.1 (M+Na)$^+$.

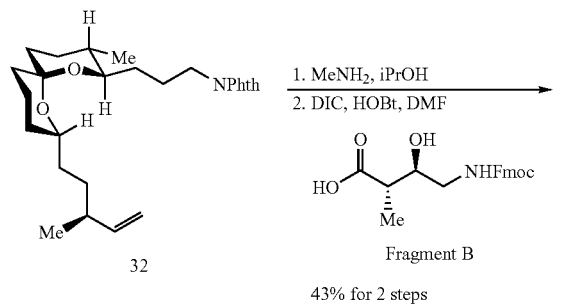

Amide 47. A solution of alkene 32 (282 mg, 0.64 mmol) in i-PrOH (10 ml) was treated with MeNH$_2$ (4 ml, 40 wt % in H$_2$O). The reaction was stirred at room temperature overnight and concentrated under reduced pressure. The residue was partitioned between 1.2 M HCl (10 ml) and Et$_2$O (10 ml). The layers were separated, and the aqueous layer was neutralized with 2 M NaOH to pH 7 and extracted with EtOAc (5×20 mL). The solution was concentrated to give the expected amine (156 mg, 80% yield). A portion of this compound (25 mg, 0.08 mmol) was treated with a solution of known fragment B (36 mg, 0.10 mmol), DCC (21 mg, 0.10 mmol), HOBt (13 mg, 0.10 mmol) in DMF (3 ml). The reaction was stirred overnight and concentrated. The residue was purified by flash column chromatography (elution with 100% EtOAc) to give amide 47 (28 mg, 53% yield). $^1$H NMR (400 MHz, CDCl$_3$) δ 0.80 (d, 3H, J=6 Hz), 0.99 (d, 3H, J=7 Hz), 1.03-1.87 (m, 14H), 1.28 (d, 3H, J=5 Hz), 1.93 (dd, 1H, J=12, 3 Hz), 2.16-2.19 (m, 1H), 2.23-2.28 (m, 1H), 3.12-3.17 (m, 2H), 3.21-3.35 (m, 2H), 3.40-3.47 (m, 3H), 3.65-3.69 (m, 1H), 4.09-4.15 (m, 1H), 4.19 (t, 1H, J=7 Hz), 4.31-4.43 (m, 3H), 4.87-4.96 (m, 2H), 5.29 (br t, 1H, J=6 Hz), 5.70 (ddd, 1H, J=17, 10, 7 Hz), 6.17-6.21 (m, 1H), 7.31 (t, 2H, J=7 Hz), 7.40 (t, 2H, J=7 Hz), 7.58 (d, 2H, J=7 Hz), 7.76 (d, 2H, J=7 Hz); $^{13}$C NMR (100 MHz, CDCl$_3$) δ 15.7, 17.9, 19.2, 20.0, 24.9, 25.5, 27.8, 30.2, 31.3, 32.6, 33.9, 34.8, 36.1, 37.6, 39.6, 42.7, 47.2, 49.1, 66.7, 69.1, 73.5, 74.3, 95.5, 112.5, 120.0, 125.0, 127.0, 127.7, 141.3, 143.8, 144.7, 156.9, 175.5; MS calculated for C$_{39}$H$_{54}$N$_2$O$_6$ (M)$^+$ 646.41, found 647.3 (M+H)$^+$.

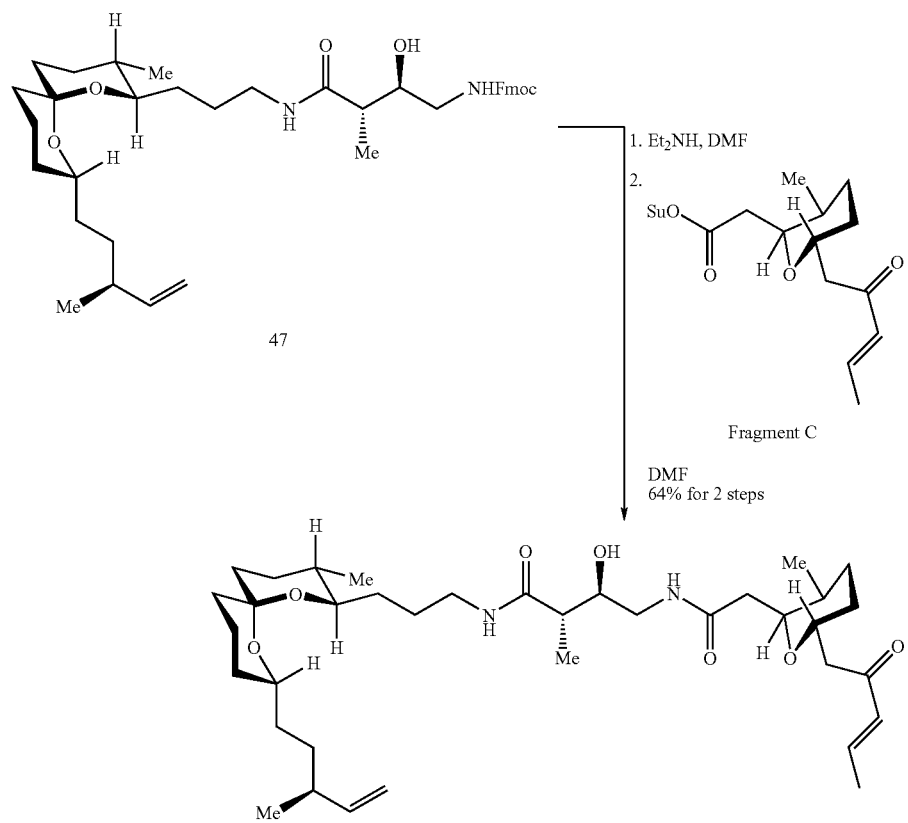

Analog 2. A solution of amide 47 (3.3 mg, 5.1 μmol) in DMF (250 μl) was treated with Et₃N (70 μl). The reaction mixture was stirred for 1 h at 20° C. and concentrated. The resulting amine was dissolved in DMF (400 μl) and treated with fragment C (4 mg, 11.8 μmol) overnight. Solvent was removed under reduced pressure. The residue was purified by column chromatography (elution with 20:1 EtOAc:MeOH) to give analog 2 (2.1 mg, 64% yield). $^1$H NMR (400 MHz, CDCl₃) δ 0.81 (δ, 3H, J=6 Hz), 0.86 (d, 3H, J=7 Hz), 0.99 (d, 3H, J=7 Hz), 1.15-2.05 (m), 1.26 (d, 3H, J=7 Hz), 1.92 (dd, 3H, J=2, 7 Hz), 2.12 (m, 2H), 2.38 (m, 1H), 2.52 (dd, 1H, J=3, 17 Hz), 2.76 (dd, 1H, J=12, 15 Hz), 2.90 (dd, 1H, J=9, 17 Hz), 3.13 (m, 1H), 3.19-3.15 (m, 3H), 3.4-3.57 (m, 2H), 3.74 (m, 1H), 4.06 (dd, 1H, J=5, 12 Hz), 4.19 (t, 1H, J=9 Hz), 4.80-4.99 (m, 2H), 5.70 (ddd, 1H, J=7, 10, 17 Hz), 6.12 (dd, 1H, J=2, 16 Hz), 6.90 (m, 1H), 6.95 (br s, 1H), 7.31 (br s, 1H). $^{13}$C NMR (100 MHz, CDCl₃) δ 15.5, 17.1, 17.9, 18.3, 19.1, 20.0, 25.7, 26.4, 27.8, 29.6, 30.4, 30.7, 31.3, 32.1, 32.5, 33.2, 33.9, 34.7, 35.4, 36.0, 37.6, 39.5, 43.1, 44.6, 45.2, 64.6, 69.0, 73.3, 74.2, 74.7, 95.3, 112.4, 132.0, 144.5, 144.7, 175.1, 198.8; MS calculated for (M)⁺ 646.46, found 647.3 (M+H)⁺.

Analog 4. A solution of amide 47 (26 mg, 0.04 mmol) in DMF (1 ml) was treated with Et₂NH (0.04 mL, 0.4 mmol). The reaction mixture was stirred for 30 min and concentrated. The resulting amine was dissolved in 1 mL of DMF and treated with a solution of acid 44 (13 mg, 0.07 mmol), DIPEA (9 μL, 0.05 mmol) and pyBOP (33 mg, 0.06 mmol) in 0.5 mL of DMF. The reaction was stirred at 20° C. for 45 min and concentrated. The residue was purified by column chromatography (elution with 95:5 CH₂Cl₂/MeOH) to give analog 4 (15 mg, 64% yield). $^1$H NMR (400 MHz, CDCl₃) δ 0.81 (d, 3H, J=6 Hz), 0.99 (d, 3H, J=7 Hz), 1.09-1.85 (m, 25H), 1.26 (d, 3H, J=7 Hz), 2.12 (quintet, 1H, J=7 Hz), 2.15-2.24 (m, 2H), 2.32 (qd, 1H, J=4, 3 Hz), 2.55-2.62 (m, 2H), 3.08-3.18 (m, 2H), 3.23-3.33 (m, 2H), 3.41-3.47 (m, 1H), 3.47-3.56 (ddd, 1H, J=14, 7, 5 Hz), 3.59-3.64 (m, 1H), 3.85-3.92 (m, 1H), 4.01-4.06 (m, 1H), 4.50 (br s, 1H), 4.90-4.97 (m, 2H), 5.07-5.11 (m, 2H), 5.68-5.84 (m, 2H), 6.53 (br t, 1H, J=5 Hz), 7.12 (br t, 1H, J=5 Hz); $^{13}$C NMR (100 MHz, CDCl₃) δ 15.6, 18.0, 18.1, 19.1, 20.1, 25.7, 27.8, 28.8, 30.3, 31.3, 32.6, 33.9, 34.8, 35.4, 36.1, 36.9, 37.7, 39.6, 41.0, 43.1, 44.1, 67.6, 69.1, 71.6, 73.9, 74.3, 95.5, 112.5, 117.2, 135.2, 144.7, 172.5, 175.3, 203.2; MS calculated for $C_{34}H_{58}N_2O_6$ (M)⁺ 590.43, found 625.2 (M+Cl)⁺.

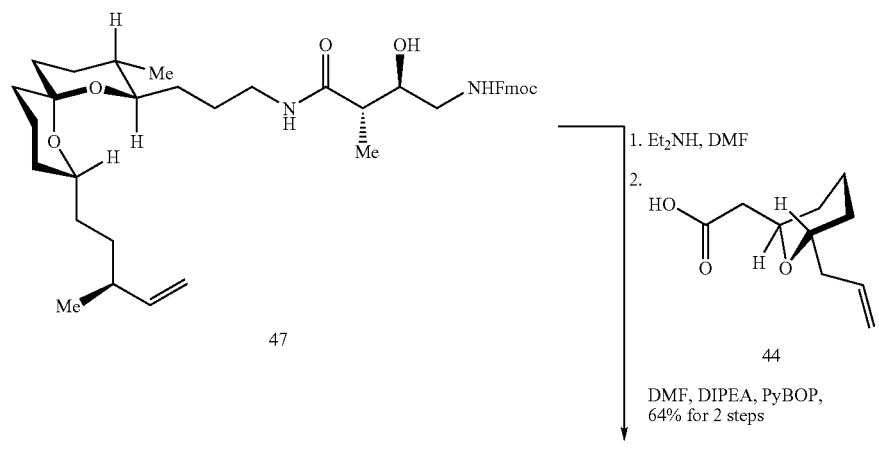

DMF, DIPEA, PyBOP,
64% for 2 steps

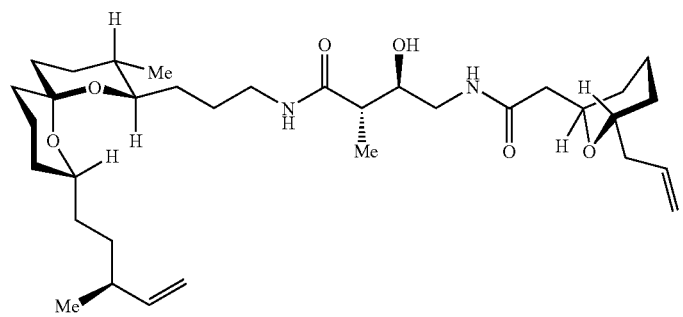

Analog 4

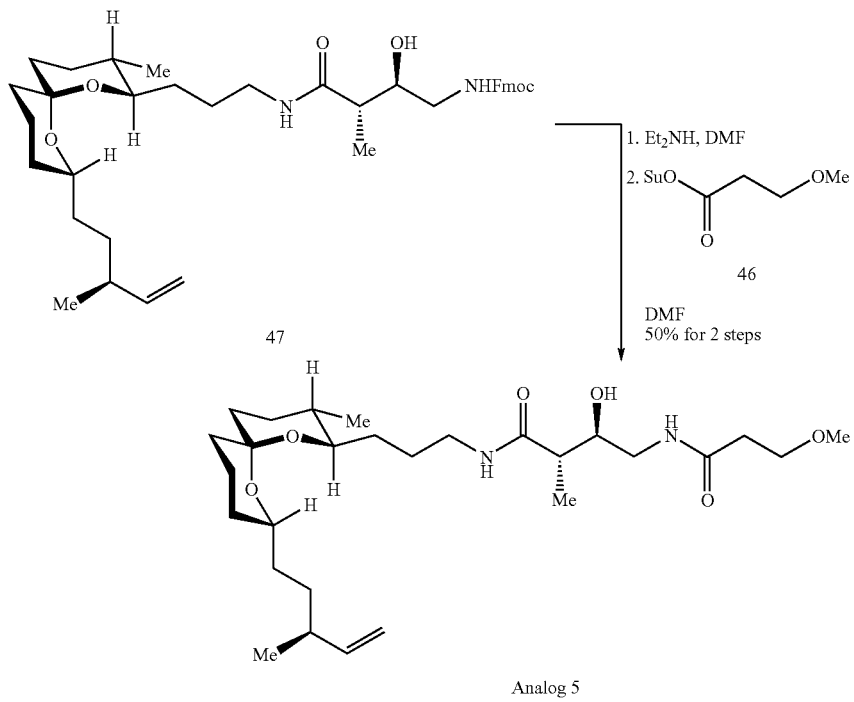

Analog 5

Analog 5. The title compound was prepared in 50% yield for 2 steps according to the protocol described above for the preparation of analog 2. $^1$H NMR (400 MHz, CDCl$_3$) δ 0.82 (d, 3H, J=6 Hz), 0.99 (d, 3H, J=7 Hz), 1.11-1.1.63 (m, 21H), 1.27 (d, 3H, J=7 Hz), 2.08-2.11 (m, 1H), 2.29-2.34 (m, 1H), 2.47 (t, 2H, J=6 Hz), 3.13-3.17 (m, 2H), 3.29-3.32 (m, 2H), 3.37 (s, 3H), 3.40-3.46 (m, 1H), 3.56 (ddd, 1H, J=13, 7, 4 Hz), 3.63 (t, 2H, J=6 Hz), 3.65-3.67 (m, 1H), 4.90-4.97 (m, 2H), 5.68 (ddd, 1H, J=17, 10, 7 Hz), 6.34-6.37 (m, 1H), 6.66-6.69 (m, 1H); $^{13}$C NMR (100 MHz, CDCl$_3$) δ 15.6, 18.0, 19.2, 20.1, 25.5, 27.8, 30.3, 31.3, 32.7, 33.9, 34.8, 35.4, 36.1, 36.8, 37.7, 39.7, 42.9, 44.1, 58.9, 68.5, 69.1, 73.4, 74.3, 95.5, 112.5, 144.7, 172.5, 175.7; MS calculated for C$_{28}$H$_{50}$N$_2$O$_6$ (M)$^+$ 510.37, found 511.2 (M+H)$^+$.

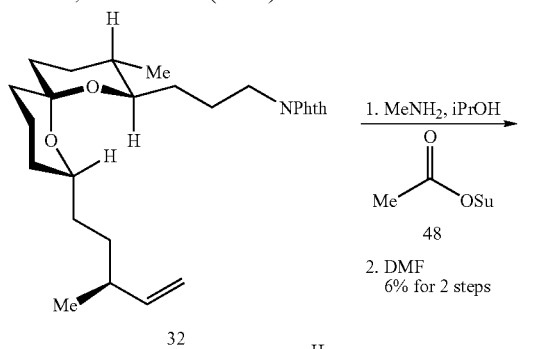

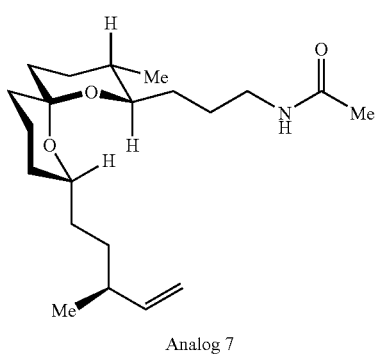

Analog 7

Analog 7. The title compound was prepared according to the procedures used for preparation of amide 22 and analog 2. $^1$H NMR (400 MHz, CDCl$_3$) δ 0.82 (d, 3H, J=7 Hz), 0.99 (d, 3H, J=7 Hz), 1.15-1.87 (m, 26H), 1.98 (s, 3H), 2.12 (quintet, 1H, J=7 Hz), 3.16 (td, 1H, J=2, 10 Hz), 3.28 (m, 2H), 3.44 (br s, 1H), 4.89-4.97 (m, 2H), 5.66 (br s, 1H), 5.70 (m, 1H). $^{13}$C NMR (100 MHz, CDCl$_3$) δ 18.1, 19.3, 20.2, 23.5, 25.8, 27.9, 30.5, 31.4, 32.7, 34.1, 35.0, 35.6, 36.3, 37.8, 40.2, 69.3; 74.5, 95.7, 112.6, 144.9, 170.2; MS calculated for C$_{21}$H$_{37}$NO$_3$ (M)$^+$ 351.28, found 352.3 (M+H)$^+$

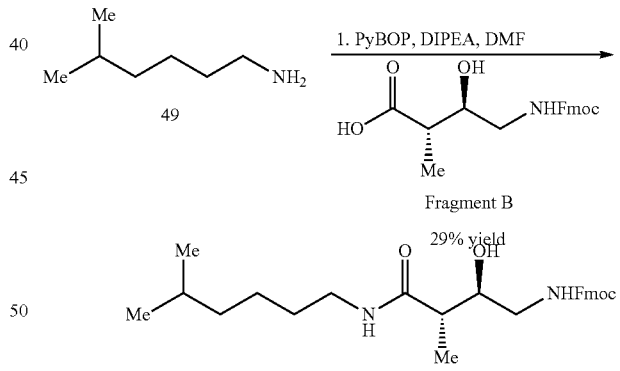

Fragment B

Amide 50. A solution of fragment B (227 mg, 0.64 mmol) in DMF (6 ml) was treated sequentially with (i-Pr)$_2$NEt (0.22 mL, 1.28 mmol), pyBOP (0.338 g, 0.65 mmol) and amine 49 (0.074 g, 0.64 mmol). The reaction was stirred at 20° C. for 2 h, concentrated and purified by flash column chromatography on silica gel (elution with Et$_2$O) to give 50 (85 mg, 29% yield). $^1$H NMR (500 MHz, CDCl$_3$) δ 0.85 (d, 6H, J=7 Hz), 1.18 (m, 2H), 1.30 (m, 5H), 1.48 (m, 3H), 2.27 (m, 1H), 3.18 (m, 1H), 3.24 (m, 2H), 3.41 (m, 1H), 3.66 (m, 1H), 4.20 (m, 1H), 4.27 (d, 1H, J=6 Hz), 4.40 (m, 2H), 5.25 (br s, 1H), 6.02 (br s, 1H), 7.32 (t, 2H, J=7 Hz), 7.40 (t, 2H, J=7 Hz), 7.59 (d, 2H, J=7 Hz), 7.76 (d, 2H, J=7 Hz); $^{13}$C NMR (100 MHz, CDCl$_3$) δ 15.8, 22.5, 24.6, 27.8, 29.7, 38.5, 39.4, 42.6, 45.2, 47.2, 66.7, 73.6, 120.0, 125.0, 127.0, 127.7, 141.3, 143.8, 157.0, 171.7; MS calculated for $C_{27}H_{36}N_2O_4$ (M)$^+$ 452.28, found 453.3 (M+H)$^+$.

6H, J=7 Hz), 1.19 (m, 2H), 1.27 (d, 3H, J=7 Hz), 1.28 (m, 2H), 1.50 (m, 3H), 2.31 (qd, 1H, J=7, 4 Hz), 2.47 (t, 2H, J=6 Hz), 3.17 (ddd, 1H, J=14, 7, 5 Hz), 3.37 (s, 3H), 3.55 (ddd, 1H,

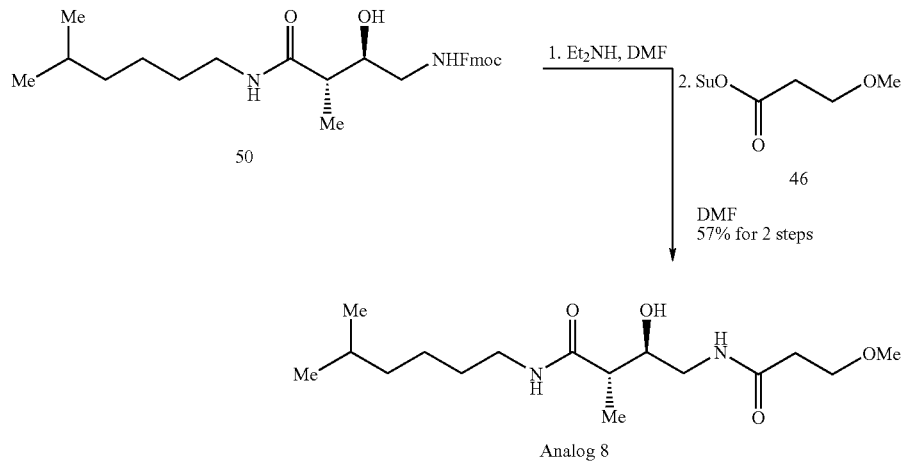

Analog 8. Amide 50 (0.045 g, 0.099 mmol) was dissolved in DMF (2 ml) and treated with Et$_2$NH (1.6 mL, 16 mmol). The reaction mixture was stirred for 1 h and concentrated. The residue was dissolved in DMF (2 mL) and treated with succinimide 46 (0.033 g, 0.16 mmol). After 12 h, the mixture was concentrated and purified by flash column chromatography on silica gel (elution with 9:1 EtOAc:MeOH) to give analog 8 (18 mg, 57% yield). $^1$H NMR (500 MHz, CDCl$_3$) δ 0.86 (d, J=14, 7, 5 Hz), 3.63 (t, 2H, J=6 Hz), 4.44 (d, 1H, J=6 Hz), 6.20 (br s, 1H), 6.62 (br s, 1H); $^{13}$C NMR (125 MHz, CDCl$_3$) δ 15.7, 22.5, 24.6, 29.7, 37.0, 38.5, 39.4, 43.0, 44.1, 58.9, 68.5, 73.6, 172.5, 175.4; MS calculated for $C_{16}H_{32}N_2O_4$ (M)$^+$ 316.24, found 317.2 (M+H)$^+$.

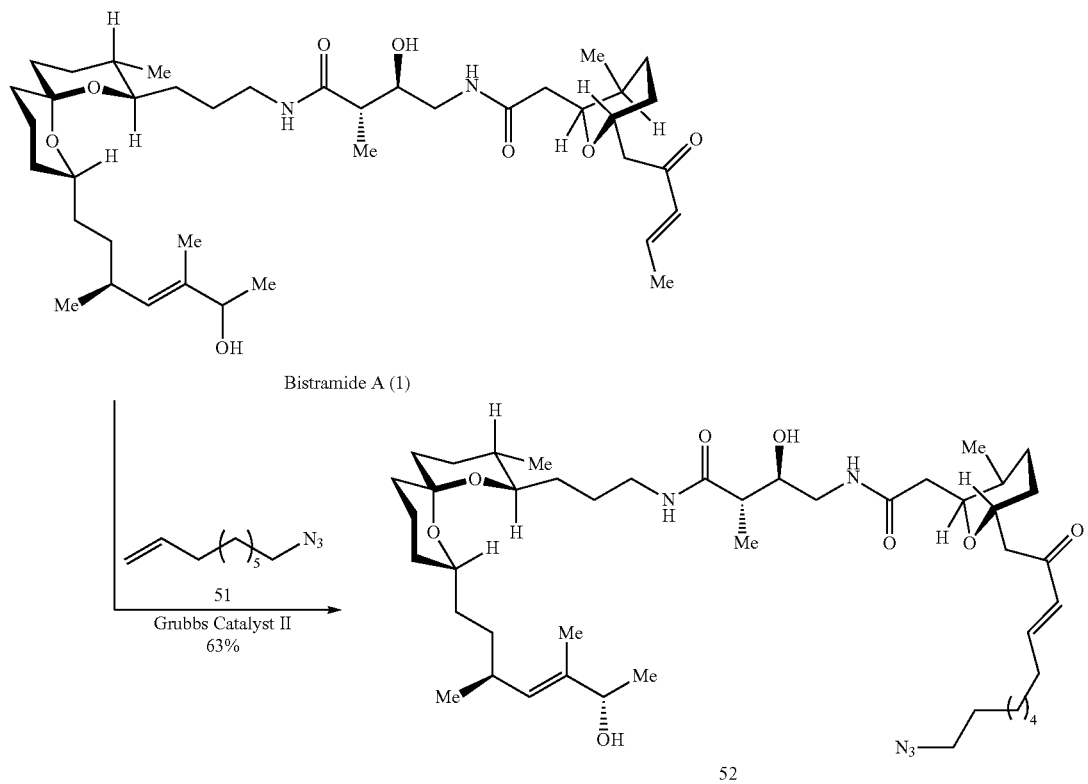

Azide 52. A solution of bistramide A (1) (8.3 mg, 11.7 μM) in CH$_2$Cl$_2$ was treated with azide 51 (1.9 mg, 11.7 μM) and Grubbs catalyst II (2 mg, 2.3 μM). The reaction mixture was heated at reflux for 1 h, concentrated and purified by flash column chromatography on silica gel (elution with 30:1-20:1 EtOAc:MeOH) to give azide 52 (4 mg, 63% based on recovered starting material). $^1$H NMR (500 MHz, CDCl$_3$) δ 0.80 (d, 3H, J=6 Hz), 0.86 (d, 3H, J=7 Hz), 0.94 (d, 3H, J=7 Hz), 1.10-1.98 (m, 44H), 2.13 (d, 1H, J=15 Hz), 2.22 (q, 2H, J=7 Hz), 2.36 (m, 2H), 2.55 (dd, 1H, J=3, 17 Hz), 2.76 (dd, 1H, J=12, 15 Hz), 2.90 (dd, 1H, J=9, 17 Hz), 3.14 (t, 1H), 3.26 (m, 4H), 3.44 (br t, 1H), 3.50 (m, 1H), 3.71 (quintet, 1H, J=5 Hz), 4.05 (dd, 1H, J=5, 11 Hz), 4.19 (br m, 2H), 4.65 (d, 1H, J=5 Hz), 5.18 (d, 1H, J=9 Hz), 6.08 (d, 1H, J=16 Hz), 6.87 (dt, 1H, J=7, 16 Hz), 6.98 (br t, 1H), 7.38 (br t, 1H); $^{13}$C NMR (125 MHz, CDCl$_3$) δ 11.7, 15.3, 17.1, 17.9, 19.1, 20.9, 21.6, 25.8, 26.4, 26.5, 27.8, 28.7, 28.8, 29.0, 29.6, 30.3, 30.7, 31.2, 31.7, 32.1, 32.5, 33.3, 33.4, 34.0, 34.8, 35.4, 36.0, 39.4, 43.2, 44.7, 45.2, 51.3, 64.5, 69.0, 73.2, 73.9, 74.1, 74.8, 95.3, 130.4, 131.3, 133.0 137.1, 149.1, 174.0, 175.0); MS calculated for C$_{46}$H$_{79}$N$_5$O$_8$ (M)$^-$ 829.59, found 864.3 (M+Cl)$^-$.

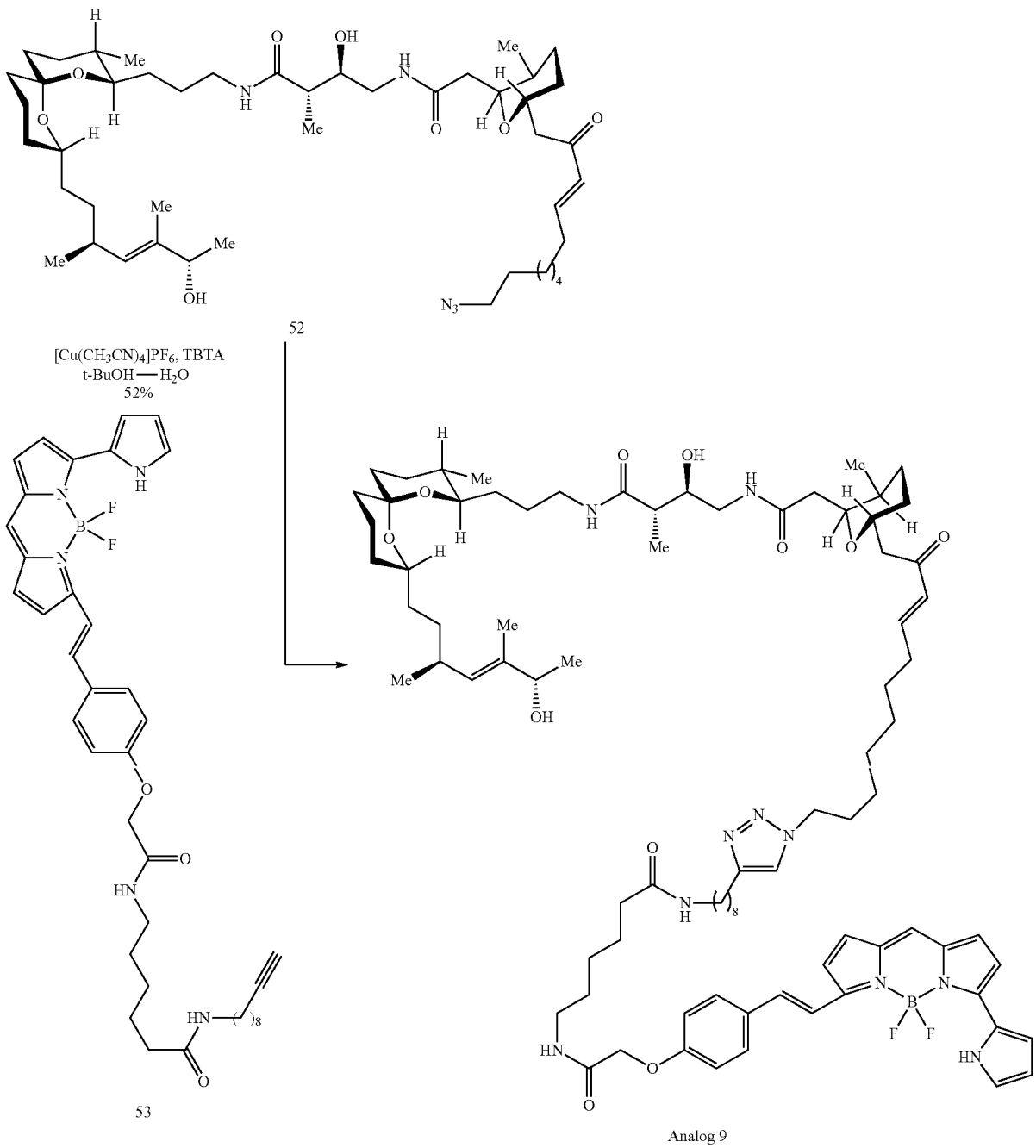

BODIPY-Bistramide Conjugate, Analog 9. The BODIPY-alkyne conjugate 53 was prepared in 90% yield by treatment of 1-amino-9-decyne (6.3 mg, 41 μmol) with BODIPY 650-665 (2 mg, 3.1 μmol, N-hydroxysuccinimide ester from Invitrogen) in DMF (0.5 ml), following removal of solvent in vacuo and purification by flash column chromatography on silica gel (elution with 20:1). Alkyne 53 (1.9 mg) was treated with azide 52 (2.3 mg, 2.7 μmol), [Cu(CH₃CN)₄]PF₆ (0.1 mg, 0.26 μmol) and TBTA (0.2 mg, 0.37 μmol) in 2:1 t-BuOH—H₂O (1.2 ml). The resulting mixture was stirred for 60 h, concentrated and purified by flash column chromatography on silica gel (elution with 12:1-8:1 EtOAc:MeOH) to give BODIPY-bistramide conjugate analog 9 (2.2 mg, 52% yield). $^1$H NMR (500 MHz, CDCl₃) selected peaks, δ 0.80 (d, 3H, J=7 Hz), 0.86 (d, 3H, J=7 Hz), 0.94 (d, 3H, J=7 Hz), 2.12 (m, 2H), 2.20 (m, 2H), 2.37 (m, 4H), 2.54 (dt, 2H, J=17, 2 Hz), 2.64 (d, 1H, J=10 Hz), 2.69 (q, 2H, J=7 Hz), 2.75 (m, 1H), 2.90 (qd, 1H, J=9, 3 Hz), 3.11-3.23 (m, 3H), 3.27 (m, 2H), 3.35 (q, 1H, J=7 Hz), 3.43 (m, 1H), 3.50 (m, 1H), 3.70 (br s, 1H), 4.05 (dd, 1H, J=7, 3 Hz), 4.19 (q, 2H, J=6 Hz), 4.30 (q, 2H, J=7 Hz), 4.53 (s, 1H), 4.67 (br s, 1H), 5.18 (d, 1H, 10 Hz), 5.51 (br s, 1H), 6.07 (d, 1H, J=16 Hz), 6.39 (br m, 1H), 6.60 (br t, 1H), 6.85 (m, 1H), 6.87 (t, 1H, J=5 Hz), 6.90-7.04 (various peaks, 3H), 7.21 (d, 1H, J=6 Hz), 7.38 (br t, 2H), 7.58 (d, 1H, J=9 Hz), 8.16 (s, 1H); MS calculated for $C_{85}H_{125}BF_2N_{10}O_{11}$ (M)⁻ 1510.96, found 1509.3 (M−H)⁻.

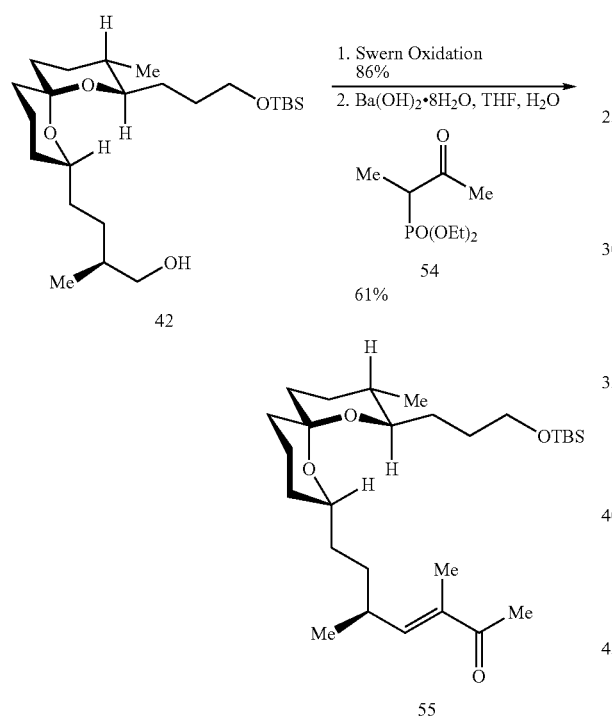

Enone 55. To a solution of oxalyl chloride (33.3 μl, 0.38 mmol) in CH₂Cl₂ (3 ml) at −78° C. was added DMSO (29.2 μl, 0.41 mmol). The reaction mixture was stirred for 5 min and treated with alcohol 42 (135.8 mg, 0.32 mmol). After 45 min, triethylamine (158.6 μl, 1.14 mmol) was added. The reaction was allowed to warm up to room temperature and Et₂O (20 ml) was added. Precipitate was filtered off and the solvent evaporated. Flash column chromatography (elution with 9:1-6:1 hexane-EtOAc) gave the aldehyde (116.2 mg, 86% yield). Ba(OH)₂.8H₂O (560.8 mg, 1.77 mmol) was heated at 125° C. under vacuum for 2 h and cooled to room temperature and suspended in THF (2.5 ml). The phosphonate 54 (221.8 mg, 1.06 mmol) was added and stirred for 10 minutes followed by the addition of a solution of the aldehyde (151.7 mg, 0.35 mmol) in THF (2.5 ml) and H₂O (0.15 ml). The reaction was stirred for 1.5 h followed by addition of CH₂Cl₂ (5 ml) and saturated NaHCO₃ (5 ml). The aqueous layer was extracted with CH₂Cl₂ (3×5 ml). The organic layers were combined, dried with MgSO₄, evaporated and flash column chromatography (elution with 15:1-9:1 hexane-EtOAc) gave enone 55 (103.7 mg, 61% yield). $^1$H NMR (500 MHz, CDCl₃); δ 0.45 (s, 6H), 0.82 (d, 3H, J=6.5 Hz), 0.88 (s, 9H), 1.33 (d, 3H, J=7 Hz), 1.20-1.58 (m, 19H), 1.75 (s, 3H), 1.72-1.90 (m, 3H), 2.29 (s, 3H), 2.55 (m, 1H), 3.11 (td, 1H, J=2, 10 Hz), 3.47 (m, 1H), 3.64 (ddt, 2H, J=6, 10, 17 Hz), 6.37 (d, 1H, J=10 Hz); $^{13}$C NMR (100 MHz, CDCl₃); δ −5.0, 11.4, 18.5, 18.8, 19.5, 20.5, 25.9, 26.4, 28.4, 29.7, 29.8, 31.8, 33.4, 34.1, 34.6, 35.5, 35.9, 36.5, 63.8, 69.2, 74.9, 95.8, 136.7, 149.7, 200.6.

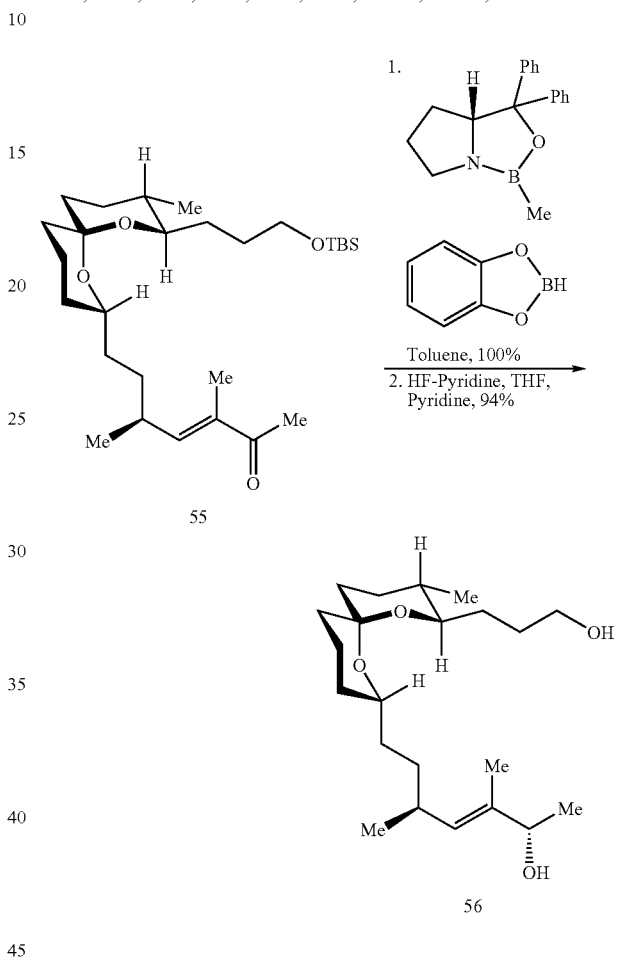

Diol 56. To a solution of the enone 55 (15.5 mg, 0.032 mmol) and (R)-2-methyl-CBS-oxazoborolidine (1 M in toluene, 35 μl, 0.035 mmol) in toluene (0.5 ml) was added catecholborane and stirred overnight at −78° C. The reaction was quenched with MeOH (100 μl). EtOAc (5 ml) was added and the organic layers were washed with satd. NaHCO₃ solution. The organic layers were dried with MgSO₄, evaporated and flash column chromatography over silica gel (elution with 6:1 Hexane-EtOAc) gave the desired product (15.5 mg, 100% yield).

The product obtained above (375.1 mg, 0.77 mmol) was dissolved in THF (25 ml) and treated with pyridine (4 ml) and HF-pyridine (1 ml). The reaction was stirred at room temperature for 18 h and quenched by adding Et₂O (50 ml) and satd. NaHCO₃ (50 ml). The aqueous layer was further extracted with Et₂O (30 ml×3). The organic layers were combined, dried with MgSO₄, evaporated and flash column chromatography over silica gel (elution with 2:1-1:1 Hexane-EtOAc) gave diol 56 (269.2 mg, 94% yield). $^1$H NMR (500 MHz, CDCl₃); δ 0.81 (d, 3H, J=6.5 Hz), 0.92 (d, 3H, J=6.5 Hz), 1.12 (m, 1H), 1.22 (d, 3H, J=6 Hz), 1.25-1.82 (m, 20H), 1.60 (s, 3H), 2.02 (s, 1H), 2.32 (m, 1H), 3.18 (td, 1H, J=2.5, 10 Hz), 3.44 (m, 1H), 3.64 (m, 2H), 4.17 (q, 1H, J=6.5 Hz), 5.14 (d, 1H, J=10 Hz); $^{13}$C NMR (100 MHz, CDCl$_3$); δ 11.6, 18.0, 19.1, 21.1, 21.7, 27.8, 28.6, 29.6, 31.3, 31.9, 33.5, 34.1, 34.5, 35.3, 36.2, 63.2, 69.2, 73.5, 74.6, 95.8, 131.5, 137.2. MS calculated for C$_{22}$H$_{40}$O$_4$ (M)$^+$ 368.29, found 351.2 (M−H$_2$O+H)$^+$.

Fragment A (6). To a solution of the diol 56 (269.2 mg, 0.73 mmol) in CH$_2$Cl$_2$, was added tosyl chloride (153.3 mg, 0.80 mmol) and pyridine (178.7 µl, 0.22 mmol) and stirred overnight. Reaction did not show complete consumption of the starting material and was subjected additional tosyl chloride (77 mg, 0.40 mmol) and stirred for 1 h. The solvents were then evaporated and flash column chromatography over silica gel (elution with 3:1-1:1 hexane-EtOAc) gave the tosylate of the primary alcohol (229 mg, 76% yield based on recovered starting material), which was used in the next step.

To a solution of the tosylate (277.7 mg, 0.53 mmol) obtained above in DMF (10 ml) was added potassium phthalimide (295.6 mg, 1.60 mmol) and the reaction was stirred at 50° C. for 90 minutes. The solvent was then removed by bulb-to-bulb distillation and flash column chromatography (elution with 3:1-1:1 hexane-EtOAc) afforded product 6 (265 mg, 100%). The $^1$H and $^{13}$C NMRs were found to be identical to previously reported data.

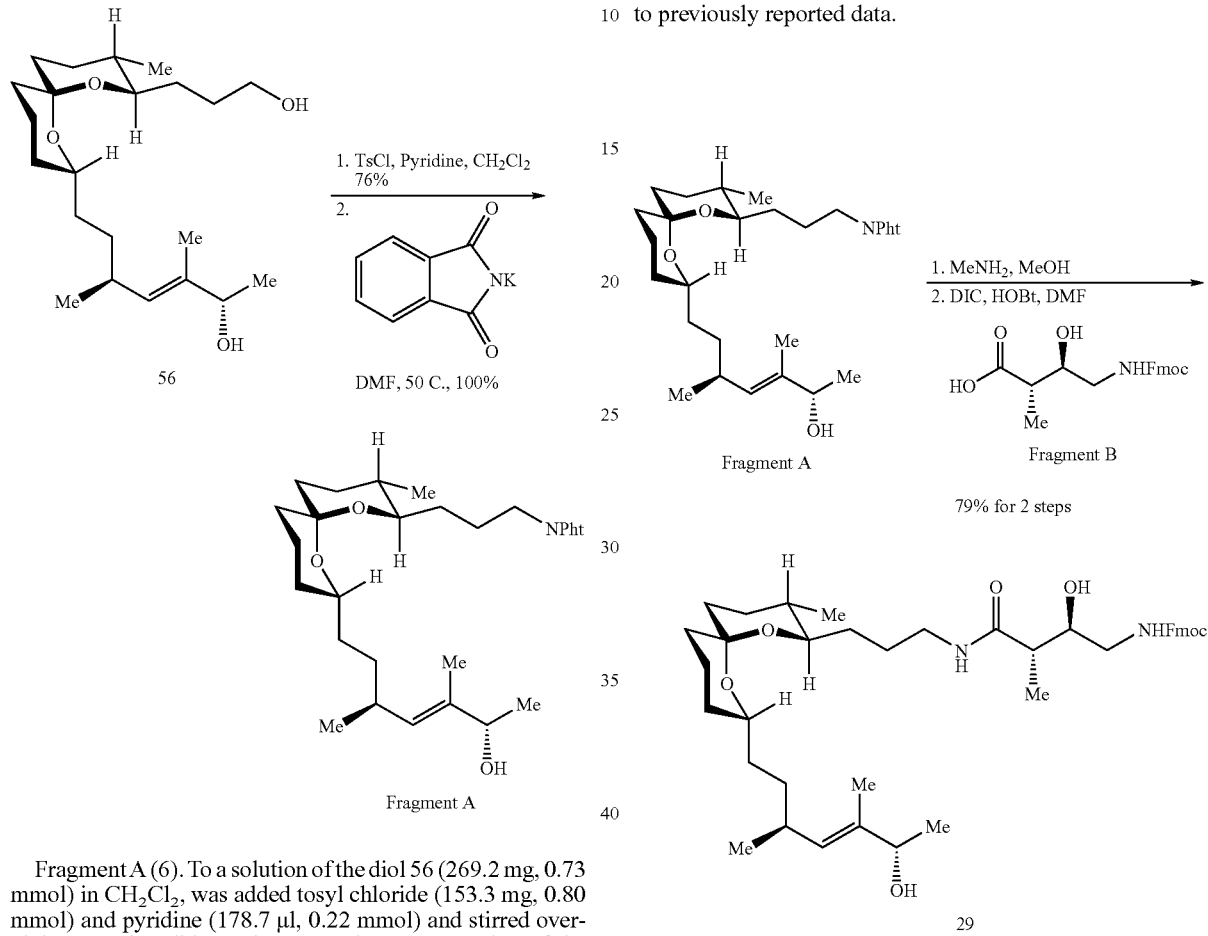

Amide 29 Amide 29 was synthesized by the method previously reported by our lab. The $^1$H and $^{13}$C NMRs were found to be identical to previously reported data.

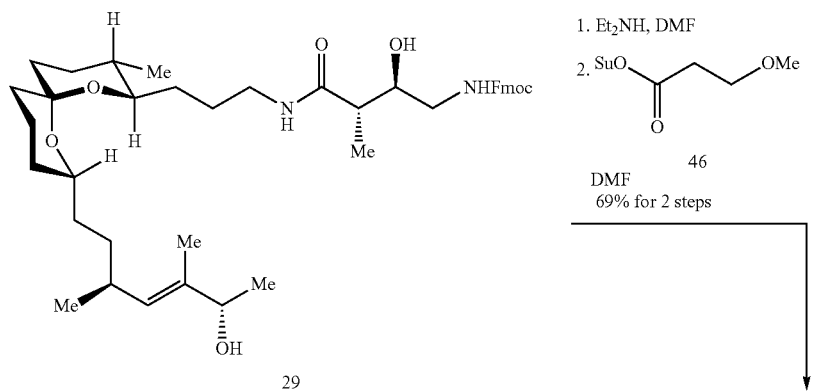

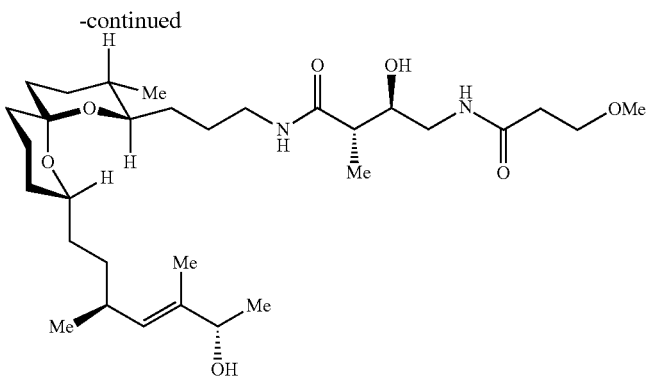

Analog 10

Analog 10. The title compound was prepared in 69% yield for 2 steps according to the protocol described above for the preparation of analog 2. $^1$H NMR (500 MHz, CDCl$_3$); δ 0.81 (d, 3H, J=7 Hz), 0.94 (d, 3H, J=6 Hz), 1.26 (d, 3H, J=6 Hz), 1.27 (d, 3H, J=7 Hz), 1.09-1.87 (m, 18H), 1.61 (s, 3H), 2.31 (m, 2H), 2.46 (t, 2H, J=6 Hz), 3.16 (m, 2H), 3.29 (q, 2H, J=6 Hz), 3.36 (s, 3H), 3.44 (m, 1H), 3.54 (m, 1H), 3.64 (t, 2H, J=5 Hz), 3.67 (m, 1H), 4.18 (q, 1H, J=6 Hz), 5.18 (d, 1H, J=9 Hz), 6.35 (br t, 1H), 6.69 (br t, 1H); $^{13}$C NMR (100 MHz, CDCl$_3$); δ 11.8, 15.6, 17.9, 19.1, 20.8, 21.7, 25.5, 27.7, 30.1, 31.2, 31.7, 33.4, 34.0, 34.7, 35.3, 36.0, 36.8, 39.4, 43.0, 44.0, 58.7, 68.4, 69.1, 73.1, 73.3, 74.1, 95.4, 131.1, 137.1, 172.3, 175.5; MS calculated for C$_{31}$H$_{56}$N$_2$O$_7$ (M)$^+$ 568.41, found 603.3 (M+Cl)$^-$.

Biochemical Characterization of Synthetic Analogs.

Cell Viability Assays. All assays were performed using at least three replicate wells for each concentration tested. Original 10-25 mM DMSO stock solution of bistramide A or its analogs was diluted to 100 µM for analogs 4-8, 10 µM for analog 3, 5 µM for analog 2 and 1 µM for bistramide A (1) with F-12K cell culture media supplemented with 10% fetal bovine serum, 100 I.U./ml penicillin, 100 µg/ml streptomycin and 2 mM L-glutamine. Two-fold serial dilutions were performed and used for cell-based assays. A549 cells were grown in 96-well white plates at the density of 1,000 cells per well in 100 µl F-12K cell culture media. Cells were allowed to attach over 24 h and treated with 30 µl of the drug solution and incubated further for 48 h. After incubation, cell viability was determined using luminescence-based commercial kit (Cell-Titer-Glo, Promega) and luminescence measured using a Wallac Victor 3 plate reader. To measure cell growth inhibition, viability assays were performed twice: at initial time point T$_0$ and after 48 h incubation (T$_{48}$). Change in the number of viable cells was measured, and GI$_{50}$ was calculated from sigmoidal plots. For analog 10, growth of A549 and PC3 cells was monitored over 96 h following addition of the drug. 100 µM was the highest concentration tested. At no point did the total DMSO conc. exceed 1%.

Isothermal Titration Calorimetry. A solution of rabbit skeletal muscle actin (5-10 µM) was titrated with bistramide A or its analog (50-100 µM) at 25° C. in buffer containing 2 mM Tris HCl, pH 8.0, 0.2 mM CaCl$_2$, 0.01% NaN$_3$, 0.2 mM ATP, 0.2 mM 2-mercaptoethanol. Dissociation constants were calculated from the binding curve using Origin analytical software (OriginLab) with the binding model involving a single set of identical sites Total Internal Reflection Fluorescence Microscopy. Actin filament severing was studied using a custom-built total internal reflection fluorescence microscope. Images were collected with a 100×, 1.45 NA objective (Olympus) and an EMCCD camera (iXon, Andor Technologies). Glass flow cell (6 µl volume) was washed with 0.25 mg/ml neutravidin in F-buffer (50 mM KCl, 1 mM MgCl$_2$, 1 mM EGTA, 10 mM imidiazole, 2 mM ATP, 0.2 mM 2-mercaptoethanol, 2 min) and blocked with 1 mg/ml BSA in F-buffer (2 min). Ten microliters of 200 nM Mg$^{2+}$-F-actin (10% biotinylated, 25% labeled with maleimide-6-tetramethylrhodamine) in TIRF-buffer (50 mM KCl, 1 mM MgCl$_2$, 1 mM EGTA, 10 mM imidiazole, 2 mM ATP, 4.5 mg/ml glucose, 0.5% 2-mercaptoethanol, 4.3 mg/ml glucose oxidase, 0.7 mg/ml catalase) was added to the flowcell and incubated for 2 min. The chamber was rinsed with TIRF-buffer and imaged. Compounds were freshly diluted from their DMSO stock solutions in TIRF-buffer and were added to the chamber immediately after the start of each experiment. Images were collected at 0.2-s exposures every 3 s for 200 frames. For kinetics studies, movies of suitable length were obtained for each of the analog concentrations. Analysis was performed using ImageJ.

Fluorescent Visualization Of F-Actin In Cells. A549 cells grown on coverslips were incubated with analogs 4-8 (100 µM) analog 3 (2 µM) or analog 2 (500 nM) or bistramide A (150 nM) in F-12K cell culture medium for 2 h, fixed with 3% formaldehyde in PBS at 25° C. for 5 min and permeabilized with 0.1% Triton X-100 at 25° C. for 10 min. After washing with PBS, coverslips were stained with Alexa Fluor 488 Phalloidin and visualized by fluorescence microscopy.

Interaction Of Bistramide-Based Compounds With Actin By MALDI-TOF. A 1:1 actin-drug complex was incubated for 30 min in 2 mM Tris-HCl, pH 8.0, 0.2 mM CaCl$_2$, 0.01% NaN$_3$, 0.2 mM ATP, 1 mM 2-mercaptoethanol, diluted with deionized water to 26 µM and mixed with an equal volume of a solution of 10 mg/ml sinapinic acid in 50% CH3CN—0.1% TFA. MALDI spectra were obtained on a Voyager-DE PRO biospectrometry workstation.

Fluorescence Visualization Of Covalent Modification Of Actin In Cells. A549 cells were incubated with 5 M BODIPY-bistramide conjugate (9) in cell culture media (F-12K, 20 ml) for 3 h. Cells were trypsinised, counted (1.6×10$^7$ cells), centrifuged, washed with PBS (2×2 ml) and treated with 200 µl of lysis buffer (50 mM Pipes, pH 6.9, 50 mM NaCl, 5 mM MgCl$_2$, 5 mM EGTA, 5% glycerol, 10% protease inhibitor mixture, 0.1% Nonidet P-40, 0.1% Triton X-100, 0.1% Tween-20, 0.1% 2-mercaptoethanol, 0.001% Antifoam C). The cell suspension was sonicated for 30 s and incubated over ice for 1 h. Cellular debris were removed by centrifugation. Gel electrophoresis of the supernatant followed by imaging on a Bio-Rad Molecular Imager FX-PRO PLUS identified the fluorescently labeled protein bands (excitation and emission wavelengths were 635 and 695 nm, respectively).

Inhibition of Tumor Growth by Analog 10

A population of 22 nude athymic mice was injected subcutaneously with A549 cells (10$^7$ cells in 100 µl PBS each). A subpopulation of 12 mice was injected with analog 10 in 1% DMSO at 20 mg/kg on the 3$^{rd}$, 5$^{th}$ and 7$^{th}$ day following treatment with A549 cells. A control population of 10 mice was injected with 1% DMSO. Tumor growth was measured over 5 weeks.

While the present disclosure has been described with reference to certain embodiments, other features may be included without departing from the spirit and scope of the present invention. It is therefore intended that the foregoing detailed description be regarded as illustrative rather than limiting, and that it be understood that it is the following claims, including all equivalents, that are intended to define the spirit and scope of this invention.

In Vitro Cell Line Screening

Analog 10 was screened utilizing 60 different human tumor cell lines, representing leukemia, melanoma and cancers of the lung, colon, brain, ovary, breast, prostate, and kidney in order to show selective growth inhibition or cell killing of particular tumor cell lines. This screen is unique in that the complexity of a 60 cell line dose response produced by a given compound results in a biological response pattern which can be utilized in pattern recognition algorithms (COMPARE program. See: http://dtp.nci.nih.gov/docs/compare/compare.html). Using these algorithms, it is possible to assign a putative mechanism of action to a test compound, or to determine that the response pattern is unique and not similar to that of any of the standard prototype compounds included in the NCI database. In addition, following characterization of various cellular molecular targets in the 60 cell lines, it may be possible to select compounds most likely to interact with a specific molecular target.

The screening is a two-stage process, beginning with the evaluation of the compound against the 60 cell lines at a single dose of 10 uM. The output from the single dose screen is reported in Table 4. Since this compound showed significant growth inhibition it will be evaluated against the 60 cell panel at five concentration levels.

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drug.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin.

Following drug addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 μA of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA). Using the absorbance measurements [time zero, (Tz), control growth, (C), and test growth in the presence of drug (Ti)], the percentage growth is calculated.

TABLE 4

One Dose Mean Graph at a 10 micromolar concentration of analog 10.

| Panel/Cell Line | Growth Percent |
|---|---|
| Leukemia | |
| CCRF-CEM | 24.00 |
| HL-60(TB) | 51.51 |
| MOLT-4 | 57.48 |
| RPMI-8226 | 58.70 |
| SR | 40.40 |
| Non-Small Cell Lung Cancer | |
| A549/ATCC | 44.50 |
| EKVX | 29.10 |
| HOP-62 | 40.92 |
| NCI-H226 | 58.32 |
| NCI-H23 | 56.78 |
| NCI-H322M | 113.58 |
| NCI-H460 | 48.25 |
| NCI-H522 | 32.60 |
| Colon Cancer | |
| HCC-2998 | 66.34 |
| HCT-116 | 55.84 |
| HCT-15 | 58.89 |
| HT29 | 30.53 |
| KM12 | 73.09 |
| SW-620 | 45.90 |
| CNS Cancer | |
| SF-268 | 37.08 |
| SF-295 | 13.26 |
| SF-539 | 40.64 |
| SNB-19 | 75.95 |
| SNB-75 | 6.67 |
| U251 | 50.08 |
| Melanoma | |
| MALME-3M | 72.36 |
| M14 | 71.74 |
| MDA-MB-435 | 72.88 |
| SK-MEL-2 | 53.99 |
| SK-MEL-28 | 71.16 |
| SK-MEL-5 | 75.27 |
| UACC-257 | 72.55 |
| UACC-62 | 48.46 |
| Ovarian Cancer | |
| IGROV1 | 17.52 |
| OVCAR-3 | 83.59 |
| OVCAR-4 | 45.16 |
| OVCAR-5 | 61.79 |
| OVCAR-8 | 90.22 |
| NCI/ADR-RES | 88.16 |
| SK-OV-3 | 59.10 |
| Renal Cancer | |
| 786-0 | 50.94 |
| A498 | 1.82 |
| ACHN | 51.57 |
| CAKI-1 | −37.52 |
| RXF 393 | 26.83 |
| SN12C | 57.59 |
| TK-10 | 30.01 |
| UO-31 | 22.67 |
| Prostate Cancer | |
| PC-3 | 66.25 |
| DU-145 | 54.89 |

TABLE 4-continued

One Dose Mean Graph at a 10 micromolar concentration of analog 10.

| Panel/Cell Line | Growth Percent |
| --- | --- |
| Breast Cancer | |
| MCF7 | 62.27 |
| MDA-MB-231/ATCC | 43.18 |
| HS 578T | 46.51 |
| BT-549 | 29.35 |
| T-47D | 71.80 |
| MDA-MB-468 | 29.03 |
| Mean | 50.03 |
| Delta | 87.55 |
| Range | 151.10 |

The invention claimed is:

1. A compound of the formula (I):

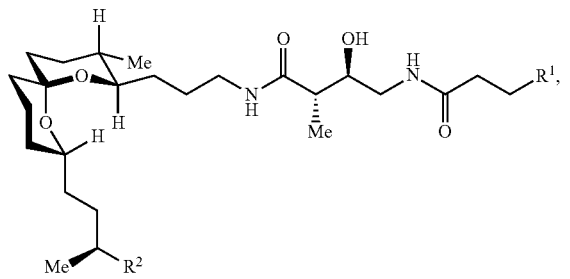

wherein $R^1$ and $R^2$ are independently selected from the group consisting of: hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, =O, $NO_2$, —$OR^8$, $OC(O)R^8$, $CO_2R^8$, —$C(O)R^8$, $C(O)NR^9R^8$, $OC(O)NR^9R^8$, $NR^{10}C(O)R^8$, $NR^{10}C(O)NR^9R^8$, $NR^9R^8$, $NR^{10}CO_2R^8$, —$SR^8$, $S(O)R^8$, $S(O)_2R^8$, $S(O)_2NR^9R^8$, $NR^{10}S(O)_2R^8$, substituted or unsubstituted $C_{6-10}$ aryl, substituted or unsubstituted 5- to 10-membered heteroaryl, $O(CH_2CHR^8)_nOCH_3$, and substituted or unsubstituted 3- to 10-membered heterocyclyl, where, each occurrence of $R^8$, $R^9$, and $R^{10}$ is independently selected from the group consisting of hydrogen, $C_{1-8}$ alkyl, $C_{2-8}$ alkenyl, $C_{2-8}$ alkynyl, aryl, $(OCH_2CH_2)_nOCH_3$, or heteroaryl; or $R^9$ and $R^8$ or $R^{10}$ and $R^8$, together with the atom(s) to which they are attached, form an substituted or unsubstituted 5-, 6-, or 7-membered ring, and where n is from 0 to 15.

2. A compound of the formula (II):

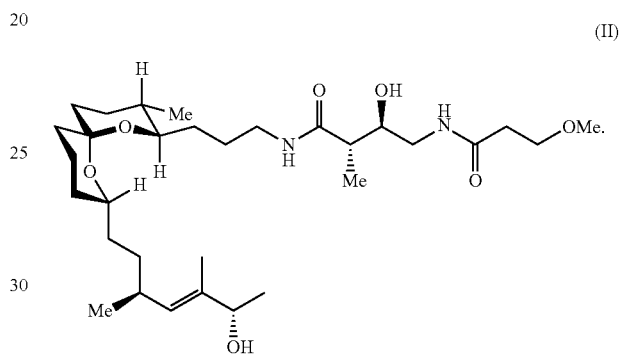

* * * * *